United States Patent
Notte

(10) Patent No.: US 10,307,427 B2
(45) Date of Patent: Jun. 4, 2019

(54) APOPTOSIS SIGNAL-REGULATING KINASE INHIBITORS

(71) Applicant: Gilead Sciences, Inc., Foster City, CA (US)

(72) Inventor: Gregory Notte, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/927,948

(22) Filed: Mar. 21, 2018

(65) Prior Publication Data

US 2018/0303844 A1   Oct. 25, 2018

Related U.S. Application Data

(63) Continuation of application No. 15/357,878, filed on Nov. 21, 2016, now Pat. No. 9,943,521, which is a continuation of application No. 14/711,331, filed on May 13, 2015, now abandoned, which is a continuation of application No. 14/135,812, filed on Dec. 20, 2013, now Pat. No. 9,051,313.

(60) Provisional application No. 61/740,777, filed on Dec. 21, 2012.

(51) Int. Cl.
| | |
|---|---|
| C07D 417/14 | (2006.01) |
| A61K 31/5377 | (2006.01) |
| A61K 31/4439 | (2006.01) |
| C07D 409/14 | (2006.01) |
| C07D 413/14 | (2006.01) |

(52) U.S. Cl.
CPC ...... *A61K 31/5377* (2013.01); *A61K 31/4439* (2013.01); *C07D 409/14* (2013.01); *C07D 413/14* (2013.01); *C07D 417/14* (2013.01)

(58) Field of Classification Search
CPC .................................................. C07D 233/56
See application file for complete search history.

(56) References Cited

U.S. PATENT DOCUMENTS

| | | |
|---|---|---|
| 7,799,782 B2 | 9/2010 | Munson et al. |
| 9,051,313 B2 | 6/2015 | Notte |
| 9,169,243 B2 | 10/2015 | Notte |
| 9,908,875 B2 | 3/2018 | Notte |
| 2007/0167386 A1 | 7/2007 | Otsu et al. |
| 2007/0276050 A1 | 11/2007 | Koch et al. |
| 2010/0144793 A1 | 6/2010 | Froestl et al. |
| 2011/0009410 A1 | 1/2011 | Corkey et al. |
| 2012/0004267 A1* | 1/2012 | Corkey ............... C07D 409/14 514/333 |
| 2012/0225880 A1 | 9/2012 | Jiaang et al. |

FOREIGN PATENT DOCUMENTS

| | | |
|---|---|---|
| WO | WO-2009/027283 | 3/2009 |
| WO | WO-2012/003387 | 1/2012 |

OTHER PUBLICATIONS

Hattori et al., "The roles of ASK family proteins in stress responses and diseases." 2009, Cell Comm. Signal. 7:1-10.
Ichijo et al., "Induction of Apoptosis by ASK1, a mammalian MAPKKK that activates SAPK/JNK and P38 signaling pathways." Science. 1997, 275, 90-94.
International Preliminary Report on Patentability for International Application No. PCT/US2013/076811 dated Jun. 23, 2015.
International Search Report and Written Opinion for International Application No. PCT/US2013/076811 dated Feb. 21, 2014. (8 pages).
Iriyama et al., "ASK1 and ASK2 differentially regulate the counteracting roles of apoptosis and inflammation in tumorigenesis." EMBO J. 2009, 28(7):843-853.
Kumar et al., "P38 MAP Kinases: Key Signalling Molecules as Therapeutic Targets for Inflammatory Diseases", 2003, Nature Review Drug Discovery, 2:717-726.
Nagai et al., "Pathophysiological roles of ASK1-MAP kinase signaling pathways." J Biochem Mol Biol. 2007, 40(1):1-6.
Office Action and Search Report for Chinese Application No. 201380066600.1 dated Apr. 5, 2016.
Office Action and Search Report for Taiwan Patent Application No. 102147530 dated Sep. 30, 2017. (3 pages).
Office Action for Chinese Patent Application No. 201380066600.1 dated Oct. 19, 2017. (3 pages).
Office Action for Gulf Cooperation Council Application No. 2013/26112 dated Nov. 24, 2016.

(Continued)

*Primary Examiner* — Rei Tsang Shiao
(74) *Attorney, Agent, or Firm* — Sheppard Mullin Richter & Hampton LLP

(57) ABSTRACT

The present invention relates to compounds of Formula (I):

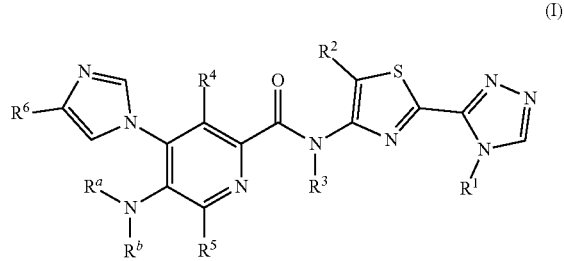

(I)

Wherein variables are as defined above. The compounds have apoptosis signal-regulating kinase ("ASK") inhibitory activity, and are thus useful in the treatment of ASK1-mediated conditions, including autoimmune disorders, inflammatory diseases, cardiovascular diseases, diabetes, diabetic nephropathy, cardio-renal diseases, including kidney disease, fibrotic diseases, respiratory diseases, COPD, idiopathic pulmonary fibrosis, acute lung injury, acute and chronic liver diseases, and neurodegenerative diseases.

1 Claim, No Drawings

(56) References Cited

OTHER PUBLICATIONS

Pimienta et al., "Canonical and Alternative MAPK Signaling." Cell Cycle. 2007, 6(21):2628-2632.
Saitoh et al., "Mammalian thioredoxin is a direct inhibitor of apoptosis signal-regulating kinase (ASK) 1." EMBO J. 1998, 17(9):2596-2606.
Takeda et al., "Apoptosis signal-regulating kinase (ASK) 2 functions as a mitogen-activated protein kinase kinase kinase in a heteromeric complex with ASK1." J Biol Chem. 2007, 282(10):7522-7531.
Takeda et al., "Apoptosis Signal-Regulating Kinase 1 in Stress and Immune Response", Annu. Rev. Pharmacol. Toxicol., 2008, 48:1-8.27.
Terada et al., "Important role of apoptosis signal-regulating kinase 1 in ischemic acute kidney injury." Biochemical and Biophysical Research Communications, 2007, 364(4):1043-1049.
Wang et al., "MAPKKK6, a Novel Mitogen-Activated Protein Kinase Kinase Kinase, That Associates with MAPKKK5." Biochem Biophys Res Commun. 1998, 253(1):33-37.
Watanabe et al., "Apoptosis signal-regulating kinase 1 is involved not only in apoptosis but also in non-apoptotic cardiomyocyte death." Biochem Biophys Res Commun. 2005, 333(2):562-567.
Zhang et al., Studies on synthesis of derivatives of 7-deaza-adenosine and their biological activities, 2003, Life Sci 74-37-43.
Zhang et al., "Suppression of apoptosis signal-regulating kinase 1-induced cell death by 14-3-3 proteins." Proc Natl Acad Sci U S A. 1999, 96(15):8511-8515.

* cited by examiner

APOPTOSIS SIGNAL-REGULATING KINASE INHIBITORS

CROSS REFERENCE TO RELATED APPLICATIONS

This application is a continuation of U.S. patent application Ser. No. 15/357,878, filed Nov. 21, 2016, now U.S. Pat. No. 9,943,521, which is a continuation of U.S. patent application Ser. No. 14/711,331, filed May 13, 2015, now abandoned, which is a continuation of U.S. patent application Ser. No. 14/135,812, filed Dec. 20, 2013, now U.S. Pat. No. 9,051,313, which application claims the benefit under 35 U.S.C. § 119(e) to U.S. Provisional Application No. 61/740,777, filed Dec. 21, 2012, the entire contents of which are incorporated herein by reference in their entirety.

FIELD OF THE INVENTION

The present invention relates to novel compounds having enzyme inhibitory activity, and to their use in the treatment of ASK1-mediated conditions, including autoimmune disorders, inflammatory diseases, including chronic kidney disease, cardiovascular diseases and neurodegenerative diseases. The invention also relates to methods for their preparation, and to pharmaceutical compositions containing such compounds.

BACKGROUND

Mitogen-activated protein kinase (MAPK) signaling cascades couple diverse extracellular and intracellular queues to appropriate cellular stress responses, including cell growth, differentiation, inflammation, and apoptosis (Kumar, S., Boehm, J., and Lee., J. C. (2003) Nat. Rev. Drug Dis. 2:717-726; Pimienta, G., and Pascual, J. (2007) Cell Cycle, 6: 2826-2632). MAPKs exist in three groups, MAP3Ks, MAP2Ks, and MAPKs, which are sequentially activated. MAPK3s directly respond to environmental signals and phosphorylate MAP2Ks, which in turn phosphorylate specific MAPKs. MAPKs then mediated the appropriate cellular response by phosphorylating cellular substrates, including transcription factors that regulate gene expression.

Apoptosis signal-regulating kinase 1 (ASK1) is a member of the mitogen-activated protein kinase kinase kinase ("MAP3K") family that activates the c-Jun N-terminal protein kinase ("JNK") and p38 MAP kinase (Ichijo, H., Nishida, E., Irie, K., Dijke, P. T., Saitoh, M., Moriguchi, T., Matsumoto, K., Miyazono, K., and Gotoh, Y. (1997) Science, 275, 90-94). ASK1 is activated by a variety of stimuli including oxidative stress, reactive oxygen species (ROS), LPS, TNF-α, FasL, ER stress, and increased intracellular calcium concentrations (Hattori, K., Naguro, I., Runchel, C., and Ichijo, H. (2009) Cell Comm. Signal. 7:1-10; Takeda, K., Noguchi, T., Naguro, I., and Ichijo, H. (2007) Annu. Rev. Pharmacol. Toxicol. 48: 1-8.27; Nagai, H., Noguchi, T., Takeda, K., and Ichijo, I. (2007) J. Biochem. Mol. Biol. 40:1-6). ASK1 undergoes activation via autophosphorylation at Thr838 in response to these signals and in turn phosphorylates MAP2Ks, such as MKK3/6 and MKK4/7, which then phosphorylate and activates p38 and JNK MAPKs, respectively. ASK2 is a related MAP3K that shares 45% sequence homology with ASK1 (Wang, X. S., Diener, K., Tan, T-H., and Yao, Z. (1998) Biochem. Biophys. Res. Commun. 253, 33-37. Although ASK2 tissue distribution is restricted, in some cell types ASK1 and ASK2 have been reported to interact and function together in a protein complex (Takeda, K., Shimozono, R., Noguchi, T., Umeda, T., Morimoto, Y., Naguro, I., Tobiume, K., Saitoh, M., Matsuzawa, A., and Ichijo, H. (2007) J. Biol. Chem. 282: 7522-7531; Iriyama, T., et al. (2009) Embo J. 28: 843-853) In non stressed conditions, ASK1 is kept in an inactive state through binding to its repressor Thioredoxin (Trx) (Saitoh, M., Nishitoh, H., Fuji, M., Takeda, K., Tobiume, K., Sawada, Y., Kawabata, M., Miyazono, K., and Ichijo, H. (1998) Embo J. 17:2596-2606), and through association with AKT (Zhang, L., Chen, J. and Fu, H. (1999) Proc. Natl. Acad. Sci. U.S.A 96:8511-8515).

Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. (2005) BBRC 333, 562-567; Zhang et al., (2003) Life Sci 74-37-43; Terada et al. (2007) BBRC 364: 1043-49). Emerging evidence suggests that ASK2, either alone or in a complex with ASK1, may play important roles in human diseases as well. Therefore, therapeutic agents that function as inhibitors of ASK1 and ASK2 signaling complexes have the potential to remedy or improve the lives of patients suffering from such conditions.

U.S. Publication No. 2007/0276050 describes methods for identifying ASK1 inhibitors useful for preventing and/or treating cardiovascular disease and methods for preventing and/or treating cardiovascular disease in an animal. The methods comprise administering to the animal an ASK1 inhibitor and, optionally, a hypertensive compound.

U.S. Publication No. 2007/0167386 reports a drug for at least one of prevention and treatment of cardiac failure containing a compound that inhibits a functional expression of ASK1 protein in a cardiomyocyte, and a method for screening the drug.

WO2009027283 discloses triazolopyridine compounds, methods for preparation thereof and methods for treating autoimmune disorders, inflammatory diseases, cardiovascular diseases and neurodegenerative diseases.

SUMMARY OF THE INVENTION

The present invention provides novel compounds that function as ASK1 inhibitors, compositions and methods of using said novel compounds. In a first aspect, the invention relates to compounds of Formula (I):

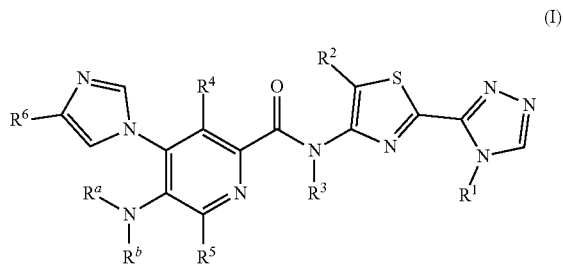

wherein:
$R^1$ is $C_1$-$C_3$ alkyl or $C_3$-$C_6$ cycloalkyl, wherein the alkyl or cycloalkyl is optionally substituted with one to three halogen atoms;

$R^2$ is hydrogen or $C_1$-$C_6$ alkyl wherein the alkyl is optionally substituted with halo.

$R^3$ is hydrogen or $C_1$-$C_3$ alkyl;

$R^4$ is hydrogen or $C_1$-$C_3$ alkyl;

$R^5$ is hydrogen, $C_1$-$C_3$ alkyl, $OR^a$ or —$NHR^a$;

$R^6$ is hydrogen, $C_1$-$C_3$ alkyl, $C_1$-$C_3$ haloalkyl, or $C_3$-$C_6$ cycloalkyl wherein the cycloalkyl is optionally substituted with $C_1$-$C_3$ alkyl, $C_1$-$C_3$ haloalkyl, or 1 or 2 halogen atoms;

$R^a$ and $R^b$ are independently hydrogen, $C_1$-$C_3$ alkyl or $R^a$ and $R^b$ combine with the nitrogen atom to which they are attached to form a four to six member heterocyclic ring optionally containing an oxygen or a nitrogen atom in the ring;

or a pharmaceutically acceptable salt or stereoisomer thereof.

In a second aspect, the invention relates to a method of using the compounds of Formula (I) in the treatment of a disease or condition in a patient, preferably a human patient, which is amenable to treatment by an ASK1 inhibitor. Such diseases include autoimmune disorders, inflammatory diseases, cardiovascular diseases (including diabetes, diabetic nephropathy, and other complications of diabetes), cardiorenal diseases, including kidney disease, fibrotic diseases, respiratory diseases (including COPD, idiopathic pulmonary fibrosis (IPF), and acute lung injury), acute and chronic liver diseases, and neurodegenerative diseases.

In a third aspect, the invention relates to pharmaceutical composition comprising a therapeutically effective amount of a compound of Formula (I) and at least one pharmaceutically acceptable excipient.

In a fourth embodiment, the invention provides a compound of formula (I) useful for treating chronic kidney disease.

In a fifth embodiment, the invention provides a compound of formula (I) useful for treating kidney fibrosis In another aspect, the disclosure provides a compound of formula (I) for use in therapy.

In another aspect, the disclosure relates to the use of a compound of formula (I) for the manufacture of a medicament for treating autoimmune disorders, inflammatory diseases, cardiovascular diseases (including diabetes, diabetic nephropathy, and other complications of diabetes), cardiorenal diseases, including kidney disease, fibrotic diseases, respiratory diseases (including COPD, idiopathic pulmonary fibrosis (IPF), and acute lung injury), acute and chronic liver diseases, and neurodegenerative diseases.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having the indicated number of carbon atoms. This term is exemplified by groups such as methyl, ethyl, n-propyl, iso-propyl and the like.

The term "substituted alkyl" refers to:

1) an alkyl group as defined above, having 1, 2, or 3 substituents selected from the indicated groups.

The term "alkylene" refers to a diradical of a branched or unbranched saturated hydrocarbon chain, typically having from 1 to 6 carbon atoms (e.g. 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "amino" refers to the group —$NH_2$. The term substituted amino refers to an $NHR^a$ or $NR^aR^b$ group wherein $R^a$ and $R^b$ (which may be same or different) represent the substituent groups.

The term "cycloalkyl" refers to cyclic alkyl groups of from 3 to 6 carbon atoms having a single cyclic ring. Such cycloalkyl groups include, by way of example, single ring structures such as cyclopropyl, cyclobutyl, cyclopentyl, and the like.

The term "halogen" or "halo" refers to fluoro, bromo, chloro, and iodo.

The term "haloalkyl" refers to alkyl of 1-3 (or as indicated) carbon atoms substituted by 1, 2, or 3 halo atoms or as chemically permissible. Examples of haloalkyl groups include trifluoromethyl, 1,1,1-trifluropropanyl, 1,1,1-trifluoroisopropanyl.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "acylhalide" refers to the group —C(O)X where X is a halogen atom preferably chloro.

As used herein and unless otherwise defined, the terms "heterocyclyl", heterocyclic and "heterocycle" are synonymous and refer to a saturated or partially unsaturated cyclic group having a single ring and having from 1 to 6 carbon atoms and from 1 to 2 hetero atoms selected from nitrogen, sulfur, and/or oxygen within the ring. Heterocyclic groups as used herein include tetrahydrofuranyl, morpholino, piperidinyl, piperazino, dihydropyridino, and the like. The term "four to six membered heterocyclic" as used herein implies a heterocyclic group as defined above wherein the total number of ring members is four to six and adjustment is made for the number of carbon atoms based on the number of heteroatoms in the ring.

"Optional" or "optionally" means that the subsequently described event or circumstance may or may not occur, and that the description includes instances where said event or circumstance occurs and instances in which it does not.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds.

The invention also includes compounds of Formula I in which one or more hydrogen atoms attached to a carbon atom is/are replaced by deuterium. Such compounds exhibit increased resistance to metabolism, and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogen atoms have been replaced by deuterium.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

Any formula or structure given herein, including Formula I compounds, is also intended to represent unlabeled forms as well as isotopically labeled forms of the compounds.

The term "therapeutically effective amount" refers to an amount that is sufficient to effect treatment, as defined below, when administered to a mammalian patient, preferably a human patient, in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any administration of a compound of the invention or practice of the method of the invention for the purpose of
  (i) protecting against the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of the present invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines and the like. Also included are amines where the two or three substituents, together with the amino nitrogen, form a heterocyclic or heteroaryl group.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

"Pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

"Prodrug" is a compound that, upon in vivo administration, is metabolized by one or more steps or processes or otherwise converted to the biologically, pharmaceutically or therapeutically active form of the compound. For example, prodrug means a compound that is chemically designed to efficiently liberate the partent drug after overcoming biological barriers to oral delivery. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability. One of skill in the art is aware of processes for generating polymoprhs of crystalline compounds. Thus, polymorphic forms of the compounds of the invention are within the ambit of the invention.

In another embodiment the present invention provides a compound of formula (I) wherein:
$R^1$ is $C_1$-$C_3$ alkyl or $C_3$-$C_6$ cycloalkyl, wherein the alkyl or cycloalkyl is optionally substituted with one to three halogen atoms;
$R^2$ is hydrogen;
$R^3$ is hydrogen;
$R^4$ and $R^5$ are both hydrogen;
$R^6$ is $C_1$-$C_3$ alkyl, or $C_3$-$C_6$ cycloalkyl;
$R^a$ and $R^b$ are independently hydrogen or $C_1$-$C_3$ alkyl; or $R^a$ and $R^b$ combine with the nitrogen atom to which they are attached to form a four to six member heterocyclic group optionally containing an oxygen or a nitrogen atom in the ring; wherein the heterocyclic group is further optionally substituted with one or two groups independently selected from $C_1$-$C_3$ alkyl and hydroxyl;
or a pharmaceutically acceptable salt or stereoisomer thereof.

In another embodiment, the present invention provides a compound of formula (I) wherein:
$R^1$ is cyclopropyl;
$R^2$ is hydrogen;
$R^3$ is hydrogen;
$R^4$ and $R^5$ are both hydrogen;
$R^6$ is cyclopropyl;
$R^a$ and $R^b$ are both $C_1$-$C_3$ alkyl or $R^a$ and $R^b$ combined with the nitrogen atom to which they are attached to form a four to six member heterocyclic group optionally containing an oxygen atom in the ring; wherein the heterocyclic group is further optionally substituted with one or two groups selected from $C_1$-$C_3$ alkyl and hydroxyl;
or a pharmaceutically acceptable salt or stereoisomer thereof.

In another embodiment, the present invention provides a compound of formula (I) wherein:
$R^1$ is $C_1$-$C_3$ haloalkyl;
$R^2$ is hydrogen;
$R^3$ is hydrogen;
$R^4$ and $R^5$ are both hydrogen;
$R^6$ is cyclopropyl;
$R^a$ and $R^b$ are both $C_1$-$C_3$ alkyl or $R^a$ and $R^b$ combined with the nitrogen atom to which they are attached to form a four to six member heterocyclic group optionally containing an oxygen atom in the ring; wherein the heterocyclic group is further optionally substituted with one or two groups selected from $C_1$-$C_3$ alkyl and hydroxyl;
or a pharmaceutically acceptable salt or stereoisomer thereof.

In another embodiment, the present invention provides a compound of formula (I) wherein:
$R^1$ is $C_1$-$C_3$ alkyl or cyclopropyl, wherein the alkyl group is substituted with three fluoro atoms;
$R^2$ is hydrogen;
$R^3$ is hydrogen;
$R^4$ and $R^5$ are both hydrogen;
$R^6$ is cyclopropyl;
$R^a$ and $R^b$ are both $C_1$-$C_3$ alkyl or $R^a$ and $R^b$ combined with the nitrogen atom to which they are attached to form a four to six member heterocyclic group optionally containing an oxygen atom in the ring; wherein the heterocyclic group is further optionally substituted with one or two groups selected from $C_1$-$C_3$ alkyl and hydroxyl;
or a pharmaceutically acceptable salt or stereoisomer thereof.

In another aspect, the present invention provides a compound of formula (I) wherein:
$R^1$ is $C_1$-$C_3$ alkyl or cyclopropyl, wherein the alkyl group is substituted with three fluoro atoms;
$R^2$ is hydrogen;
$R^3$ is hydrogen;
$R^4$ and $R^5$ are both hydrogen;
$R^6$ is cyclopropyl;
$R^a$ and $R^b$ are both methyl; or $R^a$ and $R^b$ combine with the nitrogen atom to which they are attached to form a morpholino group or an azetidinyl group wherein the azetidinyl group is dialkylated on one carbon atom, or substituted on one carbon with hydroxyl and a methyl group; or a pharmaceutically acceptable salt or stereoisomer thereof.

In another embodiment, the present invention provides a compound of formula (I) wherein:
$R^1$ is $C_1$-$C_3$ alkyl or cyclopropyl, wherein the alkyl group is substituted with three fluoro atoms;
$R^2$ is hydrogen;
$R^3$ is hydrogen;
$R^4$ and $R^5$ are both hydrogen;
$R^6$ is cyclopropyl;
$R^a$ and $R^b$ are both $C_1$-$C_3$ alkyl or $R^a$ and $R^b$ combined with the nitrogen atom to which they are attached to form a four to six member heterocyclic group optionally containing an oxygen atom in the ring; wherein the heterocyclic group is further optionally substituted with one or two groups selected from $C_1$-$C_3$ alkyl and hydroxyl;
or a pharmaceutically acceptable salt or stereoisomer thereof.

In some embodiment, the present invention provides a compound of formula (I) wherein:
$R^1$ is $C_1$-$C_3$ alkyl or $C_1$-$C_3$ cycloalkyl, wherein alkyl or cycloalkyl is optionally substituted with one to three fluoro atoms;
$R^2$ is hydrogen;
$R^3$ is hydrogen;
$R^4$ is hydrogen;
$R^5$ is hydrogen;
$R^6$ is $C_1$-$C_3$ alkyl, $C_1$-$C_3$ haloalkyl, or $C_1$-$C_3$ cycloalkyl, wherein cycloalkyl is optionally substituted with one to two fluoro atoms;
$R^a$ and $R^b$ are combined with the nitrogen atom to which they are attached to form a heterocyclic group selected from the group consisting of azetidinyl, pyrrolidinyl, piperidinyl, piperazinyl, morpholinyl; wherein the heterocyclic group is further optionally substituted with one or two groups selected from $C_1$-$C_3$ alkyl and hydroxyl;
or a pharmaceutically acceptable salt or stereoisomer thereof.

In some embodiment, the present invention provides a compound of formula (I) wherein:
$R^1$ is methyl, ethyl, propyl, fluoromethyl, difluormethyl, trifluoromethyl, fluoroethyl, difluoroethyl, trifluoroethyl, fluoropropyl, difluoropropyl, trifluoropropyl, fluorocyclopropyl, difluorocyclopropyl, or cyclopropyl;
$R^2$ is hydrogen;
$R^3$ is hydrogen;
$R^4$ is hydrogen;
$R^5$ is hydrogen;
$R^6$ is methyl, ethyl, propyl, fluoromethyl, difluormethyl, trifluoromethyl, fluoroethyl, difluoroethyl, trifluoroethyl, fluoropropyl, difluoropropyl, trifluoropropyl, fluorocyclopropyl, difluorocyclopropyl, or cyclopropyl;
$R^a$ and $R^b$ are combined with the nitrogen atom to which they are attached to form a heterocyclic group selected from the group consisting of azetidinyl, pyrrolidinyl, piperidinyl, piperazinyl, morpholinyl; wherein the heterocyclic group is further optionally substituted with one or two groups selected from methyl, ethyl, propyl, and hydroxyl;
or a pharmaceutically acceptable salt or stereoisomer thereof.

The compounds of the invention include, but are not limited to, those compounds named below:

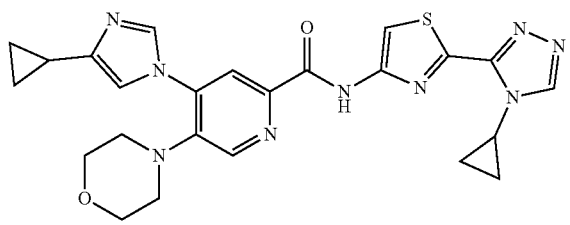

4-(4-cyclopropyl-1H-imidazol-1-yl)-N-(2-(4-cyclopropyl-4H-1,2,4-triazol-3-yl)thiazol-4-yl)-5-morpholinopicolinamide (Compound 1)

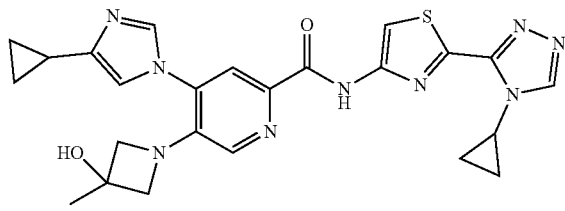 [SMILES: CC1(O)CN(c2cnc(C(=O)Nc3csc(-c4nncn4C4CC4)n3)cc2-n2cnc(C3CC3)c2)C1]

4-(4-cyclopropyl-1H-imidazol-1-yl)-N-(2-(4-cyclopropyl-4H-1,2,4-triazol-3-yl)thiazol-4-yl)-5-(3-hydroxy-3-methylazetidin-1-yl)picolinamide (Compound 2)

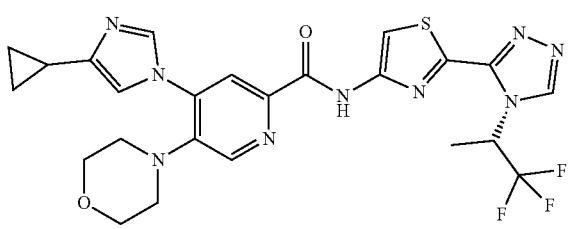

(S)-4-(4-cyclopropyl-1H-imidazol-1-yl)-5-morpholino-N-(2-(4-(1,1,1-trifluoropropan-2-yl)-4H-1,2,4-triazol-3-yl)thiazol-4-yl)picolinamide (Compound 3)

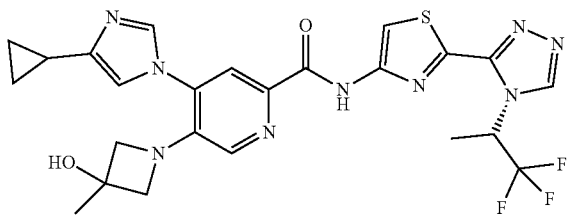

(S)-4-(4-cyclopropyl-1H-imidazol-1-yl)-5-(3-hydroxy-3-methylazetidin-1-yl)-N-(2-(4-(1,1,1-trifluoropropan-2-yl)-4H-1,2,4-triazol-3-yl)thiazol-4-yl)picolinamide (Compound 4)

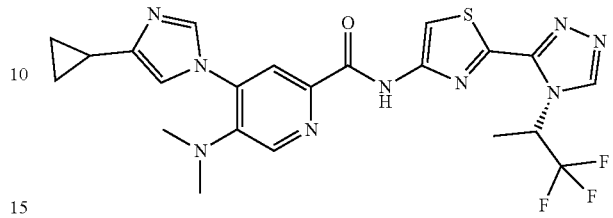

(S)-4-(4-cyclopropyl-1H-imidazol-1-yl)-5-(dimethylamino)-N-(2-(4-(1,1,1-trifluoropropan-2-yl)-4H-1,2,4-triazol-3-yl)thiazol-4-yl)picolinamide (Compound 5)

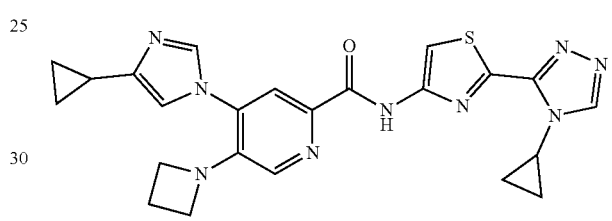

5-(azetidin-1-yl)-4-(4-cyclopropylimidazol-1-yl)-N-[2-(4-cyclopropyl-1,2,4-triazol-3-yl)-1,3-thiazol-4-yl]pyridine-2-carboxamide (Compound 6)

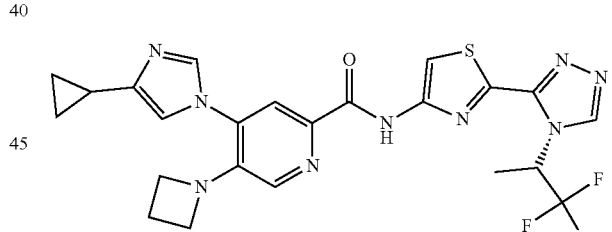

(S)-5-(azetidin-1-yl)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide (Compound 7)

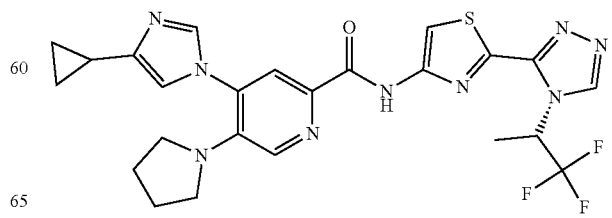

(S)-4-(4-cyclopropyl-1H-imidazol-1-yl)-5-(pyrrolidin-1-yl)-N-(2-(4-(1,1,1-trifluoropropan-2-yl)-4H-1,2,4-triazol-3-yl)thiazol-4-yl)picolinamide (Compound 8)

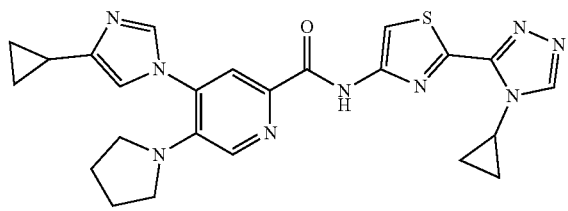 [SMILES: O=C(Nc1csc(-c2nncn2C2CC2)n1)c1cc(-n2cnc(C3CC3)c2)c(N2CCCC2)cn1]

4-(4-cyclopropylimidazol-1-yl)-N-[2-(4-cyclopropyl-1,2,4-triazol-3-yl)-1,3-thiazol-4-yl]-5-pyrrolidin-1-ylpyridine-2-carboxamide (Compound 9)

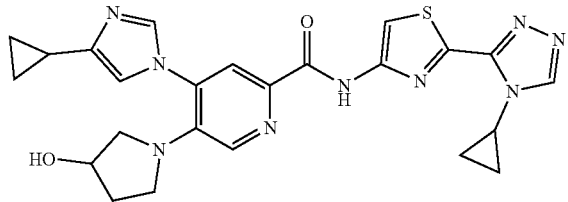 [SMILES: O=C(Nc1csc(-c2nncn2C2CC2)n1)c1cc(-n2cnc(C3CC3)c2)c(N2CCC(O)C2)cn1]

4-(4-cyclopropylimidazol-1-yl)-N-[2-(4-cyclopropyl-1,2,4-triazol-3-yl)-1,3-thiazol-4-yl]-5-(3-hydroxypyrrolidin-1-yl)pyridine-2-carboxamide (Compound 10)

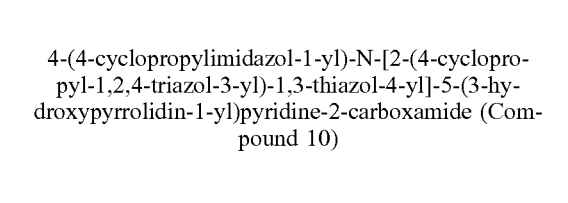

4-(4-cyclopropyl-1H-imidazol-1-yl)-5-(3-hydroxypyrrolidin-1-yl)-N-(2-(4-((S)-1,1,1-trifluoropropan-2-yl)-4H-1,2,4-triazol-3-yl)thiazol-4-yl)picolinamide (Compound 11)

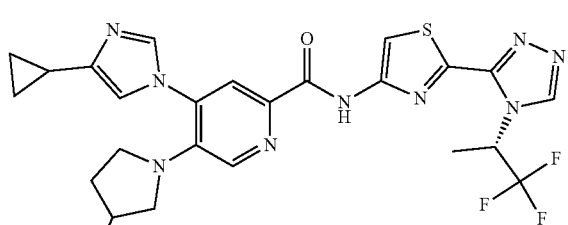

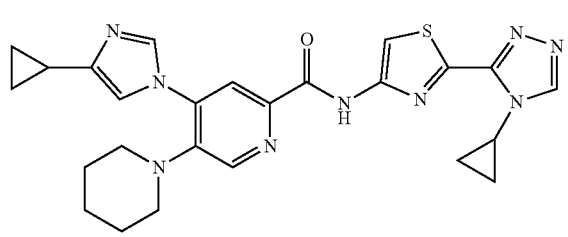 [SMILES: O=C(Nc1csc(-c2nncn2C2CC2)n1)c1cc(-n2cnc(C3CC3)c2)c(N2CCCCC2)cn1]

4-(4-cyclopropylimidazol-1-yl)-N-[2-(4-cyclopropyl-1,2,4-triazol-3-yl)-1,3-thiazol-4-yl]-5-piperidin-1-ylpyridine-2-carboxamide (Compound 12)

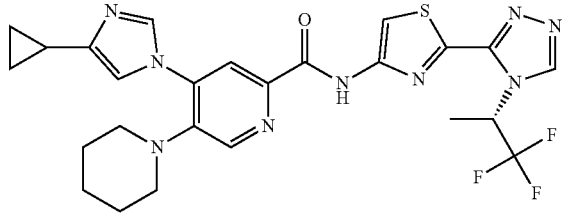 [SMILES: C[C@H](n1cnnc1-c1nc(NC(=O)c2cc(-n3cnc(C4CC4)c3)c(N3CCCCC3)cn2)cs1)C(F)(F)F]

(S)-4-(4-cyclopropyl-1H-imidazol-1-yl)-5-(piperidin-1-yl)-N-(2-(4-(1,1,1-trifluoropropan-2-yl)-4H-1,2,4-triazol-3-yl)thiazol-4-yl)picolinamide (Compound 13)

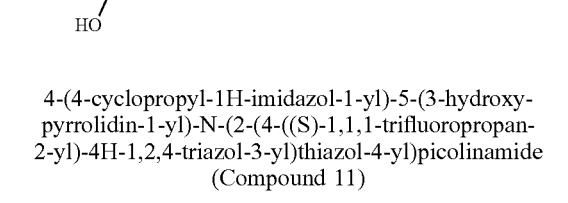

(S)-4-(4-cyclopropyl-1H-imidazol-1-yl)-5-(4-hydroxy-4-methylpiperidin-1-yl)-N-(2-(4-(1,1,1-trifluoropropan-2-yl)-4H-1,2,4-triazol-3-yl)thiazol-4-yl)picolinamide (Compound 14)

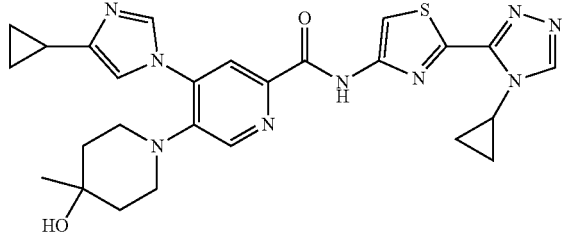 [SMILES: CC1(O)CCN(c2cnc(C(=O)Nc3csc(-c4nncn4C4CC4)n3)cc2-n2cnc(C3CC3)c2)CC1]

4-(4-cyclopropylimidazol-1-yl)-N-[2-(4-cyclopropyl-1,2,4-triazol-3-yl)-1,3-thiazol-4-yl]-5-(4-hydroxy-4-methylpiperidin-1-yl)pyridine-2-carboxamide (Compound 15)

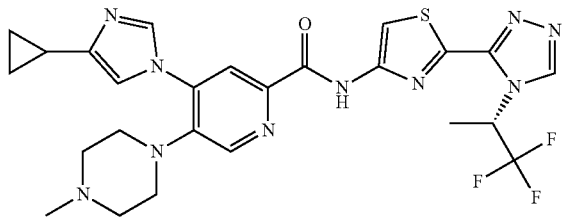 [SMILES: C[C@H](n1cnnc1-c1nc(NC(=O)c2cc(-n3cnc(C4CC4)c3)c(N3CCN(C)CC3)cn2)cs1)C(F)(F)F]

(S)-4-(4-cyclopropyl-1H-imidazol-1-yl)-5-(4-methylpiperazin-1-yl)-N-(2-(4-(1,1,1-trifluoropropan-2-yl)-4H-1,2,4-triazol-3-yl)thiazol-4-yl)picolinamide (Compound 16)

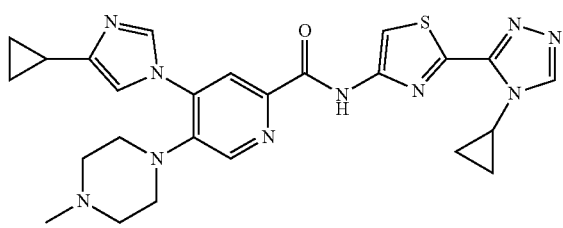 [SMILES: CN1CCN(c2cnc(C(=O)Nc3csc(-c4nncn4C4CC4)n3)cc2-n2cnc(C3CC3)c2)CC1]

4-(4-cyclopropylimidazol-1-yl)-N-[2-(4-cyclopropyl-1,2,4-triazol-3-yl)-1,3-thiazol-4-yl]-5-(4-methylpiperazin-1-yl)pyridine-2-carboxamide (Compound 17)

In one aspect, the present application provides compounds, methods and compositions that use or include a racemic mixture, a mixture containing an enantiomeric excess (e.e.) of one enantiomer, or a mixture containing a diastereomeric excess (d.e.) of one diastereomer. The compounds of formula (I) may comprise at least 1%, at least 10%, at least 20%, at least 30%, at least 40%, at least 50%, at least 60%, at least 65%, at least 70%, at least 75%, at least 80%, at least 85%, at least 90%, at least 95%, at least 98%, or at least 99% of one stereoisomer that has the desired ASK-1 activities. By way of example, all chiral amine starting materials (e.g. $R^aR^bNH$) used in general preparation of compounds of formula (I) (e.g. Compounds 3, 4, 5, 7, 8, 11, 13, 14, 16) were used as a mixture of enantiomers. In another example, Intermediate E in the general preparation of the compounds of formula (I) was prepared and used as a mixture containing predominantly (S)-4-(4-cyclopropyl-1H-imidazol-1-yl)-5-fluoro-N-(2-(4-(1,1,1-trifluoropropan-2-yl)-4H-1,2,4-triazol-3-yl)thiazol-4-yl)picolinamide.

In another aspect, the present application provides methods, compositions that use or include optical isomers, racemates, or other mixtures thereof, of the compounds of formula I or a pharmaceutically acceptable salt, prodrug, or solvate thereof. The single enantiomer or diastereomer, i.e., optically active form, may be obtained by asymmetric synthesis or by resolution of the racemate. Resolution of racemates may be accomplished, for example, by known methods such as crystallization in the presence of a resolving agent, or chromatography, using, for example a chiral high pressure liquid chromatography (HPLC) column. For example, there are Z- and E-forms (or cis- and trans-forms) of the compounds or a pharmaceutically acceptable salt, prodrug, or solvate thereof with carbon-carbon double bonds.

Nomenclature

Names of compounds of the present invention are provided using the naming system from ChemBioDraw Ultra 11 or the Molecule to Chemical Name component of Pipeline Pilot version 9.1.0 set to International Union of Pure and Applied Chemistry (IUPAC). Other compounds or radicals may be named with common names, or systematic or non-systematic names. The naming and numbering of the compounds of the invention is illustrated with a representative compound of Formula (I)

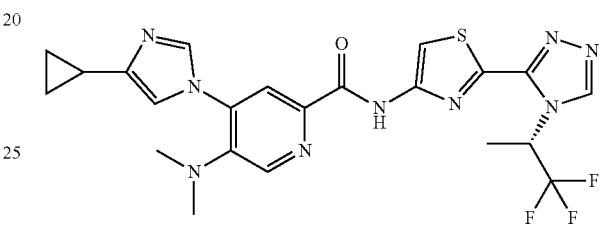

which is named: (S)-4-(4-cyclopropyl-1H-imidazol-1-yl)-5-(dimethylamino)-N-(2-(4-(1,1,1-trifluoropropan-2-yl)-4H-1,2,4-triazol-3-yl)thiazol-4-yl)picolinamide. In another example, the compound having the below structure of

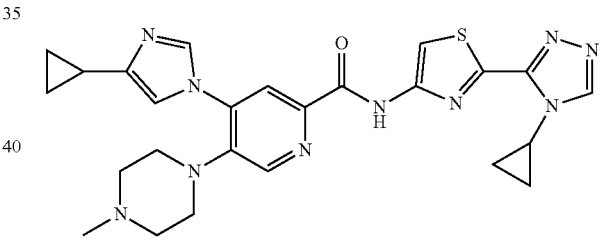

may be referred to as 4-(4-cyclopropylimidazol-1-yl)-N-[2-(4-cyclopropyl-1,2,4-triazol-3-yl)-1,3-thiazol-4-yl]-5-(4-methylpiperazin-1-yl)pyridine-2-carboxamide using the naming system of the Molecule to Chemical Name component of Pipeline Pilot version 9.1.0 set to IUPAC-style names or 4-(4-cyclopropyl-1H-imidazol-1-yl)-N-(2-(4-cyclopropyl-4H-1,2,4-triazol-3-yl)thiazol-4-yl)-5-(4-methylpiperazin-1-yl)picolinamide using the name system of ChemBioDraw Ultra.

Combination Therapy

Human patients being treated for an acute cardiovascular disease event by administration of ASK1 inhibitors often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of an ASK1 inhibitor exhibit conditions that can benefit from treatment with therapeutic agents that are antibiotics, analgesics, and/or antidepressants and anti-anxiety agents.

Cardiovascular related diseases or conditions that can benefit from a combination treatment of ASK1 inhibitors with other therapeutic agents include, without limitation, angina, including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of ASK1 inhibitors with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol, atenolol, betaxolol, bisoprolol/hydrochlorothiazide, bisoprolol, carteolol, esmolol, labetalol, metoprolol, nadolol, propranolol, sotalol (Betapace), and timolol.

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine, bepridil, diltiazem, felodipine, nifedipine, nimodipine (Nimotop), nisoldipine, verapamil, and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone, furosemide, bumetanide, spironolactone, and eplerenone.

Angiotensin converting enzyme (ACE) inhibitors reduce the workload on the heart by expanding the blood vessels and decreasing resistance to blood flow. Examples of ACE inhibitors include benazepril, captopril, enalapril, fosinopril, lisinopril, moexipril, perindopril, quinapril, ramipril, and trandolapril.

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid, ticlopidine, clopidogrel, dipyridamole, cilostazol, persantine sulfinpyrazone, dipyridamole, indomethacin, and glycoprotein llb/llla inhibitors, such as abciximab, tirofiban, and eptifibatide. Beta blockers and calcium channel blockers also have a platelet-inhibiting effect.

Anticoagulants prevent blood clots from growing larger and prevent the formation of new clots. Examples of anticoagulants include bivalirudin, warfarin, unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase, and tissue plasminogen activator.

Antiarrhythmic agents are used to treat disorders of the heart rate and rhythm. Examples of antiarrhythmic agents include amiodarone, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation.

Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

Patients in need of the ASK1 inhibitor often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline, albuterol, salmeterol, Serevent, theophylline, ipratropium bromide, tiotropium, methylprednisolone, magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Analgesics are therapeutic agents that are used to relieve pain. Examples of analgesics include opiates and morphinomimetics, such as fentanyl and morphine; paracetamol; NSAIDs, and COX-2 inhibitors.

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, and ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Synthesis of Compounds of Formula I

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula (I), may be accomplished as described in the following Scheme A and or as provided in the following examples. If available, reagents may be purchased commercially, e.g. from Sigma Aldrich or other chemical suppliers.

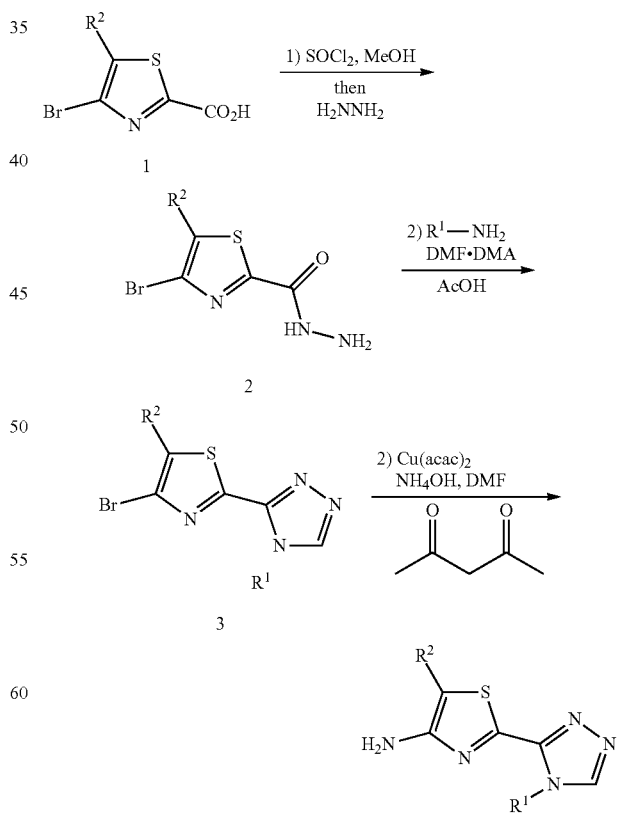

Intermediate A

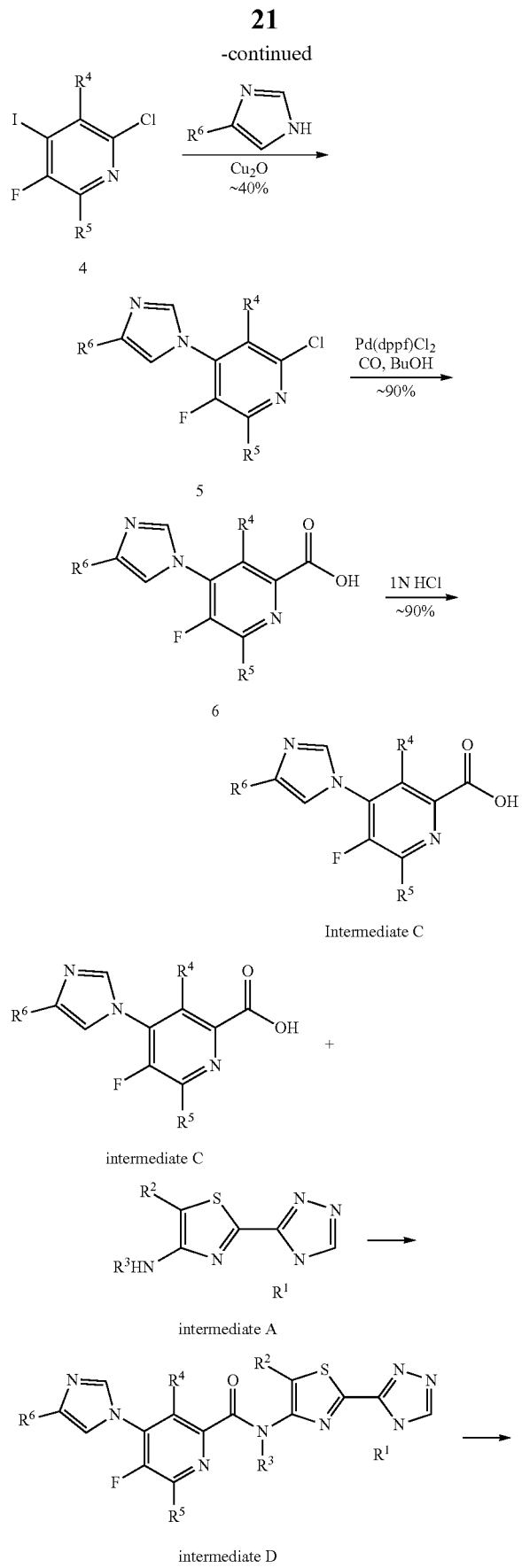

Formula (I)

The 4-bromo thiazole carboxylic acid (1) is converted to the carbohydrazide first by conversion to the acyl chloride using an acylhalide forming reagent such as thionyl chloride or oxalyl chloride. The acyl halide is then treated with hydrazine to form the carbohydrazide (2). The carbohydrazide is cyclized in the presence of dimethylformamide dimethylacetal and the appropriately substituted primary amine to afford the triazole (3) having the desired R1 substituent. Alternatively, the acyl halide is converted to the amine by reaction with an appropriately substituted amine ($R^1NH_2$) to form the corresponding amide of compound (1). The amide is converted to the thioamide by reaction with Lawesson's reagent using known conditions or as described herein. The thioamide is then reacted with hydrazine to afford the triazole (3). The triazole (3) is converted to the amino analog (intermediate A) via reaction with copper acetate and ammonium hydroxide in DMF or other solvents known to one of ordinary skill in the art.

Preparation of the intermediate C is initiated by coupling the compound (4) with an appropriately substituted imidazole having the desired $R^6$ substituent. The resulting product (5) is carbonylated using palladium reagents such as Pd(dppf)$Cl_2$ in the presence of carbon monoxide in a protic solvent such as butanol. The resulting acid (6) is isolated as intermediate C. The intermediate C is then reacted with intermediate A to form the amide intermediate D. Intermediate D is subjected to an $S_NAr$ reaction and converted to the desired amine compound of formula (I). One of ordinary skill in the art is able to perform the reactions herein following the above general scheme, the specific procedures provided herein, or other literature sources known to such an artisan.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

Preparation of 2-(4-cyclopropyl-4H-1,2,4-triazol-3-yl)thiazol-4-amine (Intermediate A)

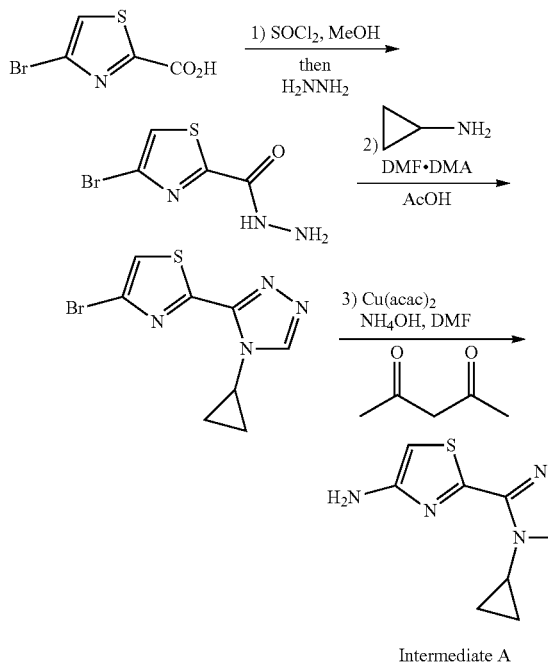

Intermediate A

Step 1: Preparation of 4-bromothiazole-2-carbohydrazide

To a solution of the 4-bromothiazole-2-carboxylic acid (2.0 g, 9.8 mmol) in MeOH (10 mL) was added SOCl$_2$ (710 µL, 9.8 mmol) and the reaction was refluxed for 3 hours. The reaction was concentrated, the residue was suspended in EtOH (10 mL), hydrazine hydrate (2.4 mL, 49 mmol) was added and the reaction was heated to reflux for 90 minutes. The reaction was concentrated, suspended in CH$_3$CN, filtered, and the solids were washed with CH$_3$CN, Et$_2$O, and dried to afford 1.7 g (77%) of 4-bromothiazole-2-carbohydrazide as a yellow solid. M+1=222.1

Step 2: Preparation of 4-bromo-2-(4-cyclopropyl-4H-1,2,4-triazol-3-yl)thiazole 4-bromothiazole-2-carbohydrazide (620 mg, 2.8 mmol) and toluene (9 mL) were added to a sealable vial, DMF-DMA (920 µL, 6.9 mmol) was added and the reaction was stirred for 5 minutes. Cyclopropyl amine (770 µL, 11 mmol), and AcOH (160 µL, 2.8 mmol) were added and the reaction was heated in a microwave reactor at 150° C. for 30 minutes. The reaction was concentrated and purified by flash chromatography (1→7% MeOH in CH$_2$Cl$_2$) to afford 740 mg of 4-bromo-2-(4-cyclopropyl-4H-1,2,4-triazol-3-yl)thiazole (contaminated with DMF-DMA, but used directly in next step).

Step 3: Preparation of 2-(4-cyclopropyl-4H-1,2,4-triazol-3-yl)thiazol-4-amine To a microwave vial was added the bromothiazole synthesized above (1.0 g, 3.7 mmol), Cu(acac)$_2$ (97 mg, 0.37 mmol), and Cs$_2$CO$_3$ (2.4 g, 7.4 mmol) and the flask was charged with N$_2$. Pentadione (150 µL, 1.5 mmol), DMF (8 mL), and ammonium hydroxide (1.1 ml, 300 µL/mmol) were added and the reaction was heated to 90° C. When the reaction was judged to be complete by HPLC (~4 hrs), the mixture was filtered through Celite, the Celite was washed with CH$_2$Cl$_2$, the filtrate was concentrated, and the residue was purified by flash chromatography (6→13% MeOH in CH$_2$Cl$_2$) to provide 480 mg (63% over two steps) of 2-(4-cyclopropyl-4H-1,2,4-triazol-3-yl)thiazol-4-amine as an oil. M+1=208.2

Preparation of 2-(4-cyclopropyl-4H-1,2,4-triazol-3-yl)thiazol-4-amine (Intermediate B)

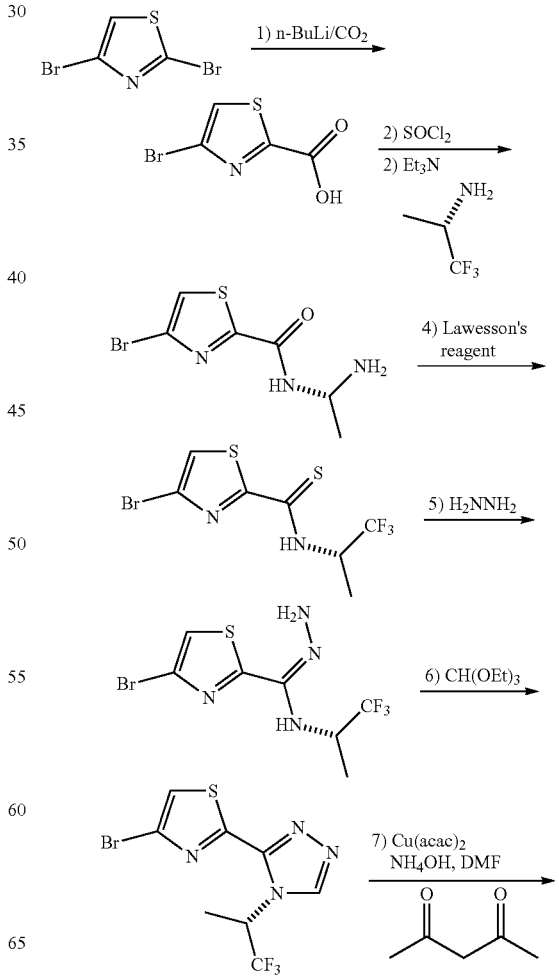

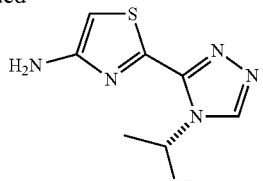

Intermediate B

Step 1: Preparation of 4-bromothiazole-2-carboxylic Acid

To the solution of 2,4-dibromothiazole (50 g, 207 mmol, 1.0 eq.) in Et20 (1000 ml) was added n-BuLi (90 ml, 2.5 M, 1.1 eq.) at −78° C. dropwise and it was stirred for one hour. The reaction solution was poured into dry $CO_2$ at −78° C. and the reaction mixture was warmed to the room temperature. TLC and LCMS showed the reaction was complete. It was quenched with water (100 ml). The Et20 phase was removed. The aqueous phase was adjusted to pH to 2-3 and extracted with ethyl acetate. The organic phase was dried, filtered and concentrated to obtain 35 g (82% y) of the 4-bromothiazole-2-carboxylic acid. $^1$HNMR (400 MHz, DMSO): δ8.23 (1H, s)

Steps 2-3: Preparation of (S)-4-bromo-N-(1,1,1-trifluoropropan-2-yl)thiazole-2-carboxamide To the mixture of 4-bromothiazole-2-carboxylic acid (80 g, 1.0 eq.) in $SOCl_2$ (300 ml) was added DMF (10 drops). It was refluxed for 5 hours and concentrated. The residue was dissolved in DCM (300 ml) and added to the solution of (S)-1,1,1-trifluoropropan-2-amine hydrochloride (60.5 g, 1.05 eq.) with Et3N (117 g, 3.0 eq.) at 0° C. It was stirred overnight. TLC and LCMS showed the reaction was complete. It was quenched with water and extracted with DCM. The organic phase was dried, filtered and concentrated. The residue was purified by column to obtain 62 g (53% y) of(S)-4-bromo-N-(1,1,1-trifluoropropan-2-yl)thiazole-2-carb oxamide.
1HNMR (400 MHz, CDCl3): δ7.47 (1H, s), 7.17 (1H, br s), 4.74-4.76 (1H, m), 1.39 (3H, d, J=6.8 Hz).

Step 4: Preparation of (S)-4-bromo-N-(1,1,1-trifluoropropan-2-yl)thiazole-2-carbothioamide To a solution of (S)-4-bromo-N-(1,1,1-trifluoropropan-2-yl)thiazole-2-carboxamide (50 g, 1.0 eq.) in toluene (1000 ml) was added Lawesson's Reagent (100 g, 1.5 eq.). It was refluxed overnight. TLC and LCMS showed the reaction was complete. It was concentrated and the residue was purified by column to obtain 46 g (88% y) of (S)-4-bromo-N-(1,1,1-trifluoropropan-2-yl)thiazole-2-carbothioamide.

Step 5: Preparation of (S)-4-bromo-N-(1,1,1-trifluoropropan-2-yl)thiazole-2-carbohydrazonamide To a solution of (S)-4-bromo-N-(1,1,1-trifluoropropan-2-yl)thiazole-2-carbothioamide (46 g, 1.0 eq.) was added hydrazine hydrate (15 g, 2.0 eq.). It was refluxed overnight. TLC and LCMS showed the reaction was complete. It was concentrated and the residue was purified by a flash column to obtain 48 g (100% y) of (S)-4-bromo-N-(1,1,1-trifluoropropan-2-yl)thiazole-2-carbohydrazonamide

Step 6: Preparation of (S)-4-bromo-2-(4-(1,1,1-trifluoropropan-2-yl)-4H-1,2,4-triazol-3-yl)thiazole (S)-4-bromo-N-(1,1,1-trifluoropropan-2-yl)thiazole-2-carbohydrazonamide (55 g,) in triethoxymethane (500 ml) was stirred at 90° C. for 3 hours and then at 130° C. overnight and the reaction was concentrated. The residue was purified by column to obtain 44 g (77% y) of (S)-4-bromo-2-(4-(1,1,1-trifluoropropan-2-yl)-4H-1,2,4-triazol-3-yl)thiazole.
$^1$HNMR (400 MHz, CDCl3): δ8.46 (1H, s), 7.43 (1H, s), 6.48-6.52 (1H, m), 1.83 (3H, d, J=7.2 Hz).

Step 7: Preparation of (S)-2-(4-(1,1,1-trifluoropropan-2-yl)-4H-1,2,4-triazol-3-yl)thiazol-4-amine (Intermediate B)

To a solution of (S)-4-bromo-2-(4-(1,1,1-trifluoropropan-2-yl)-4H-1,2,4-triazol-3-yl)thiazole (50 g, 120 mmol, 1.0 eq.) in DMF (500 ml) was added $Cu(acac)_2$ (3.2 g, 12 mmol, 0.1 eq.), acetylacetone (1.2 g, 0.1 eq.) and $NH_4OH$ (50 ml, conc). It was stirred at 90° C. overnight and it was concentrated. The residue was dissolved in MeOH (500 ml) and it was filtered. The filtrate was concentrated and the residue was purified by column to obtain 9.6 g (24% y) of Intermediate B.
$^1$HNMR (400 MHz, CDCl3): δ8.38 (1H, s), 6.58-6.65 (1H, m), 6.14 (1H, s), 4.20 (2H, br s), 1.77 (3H, d, J=7.2 Hz); ESI MS: 264 ([M+1]).

Preparation of 4-(4-cyclopropyl-1H-imidazol-1-yl)-5-fluoropicolinic Acid (Intermediate C)

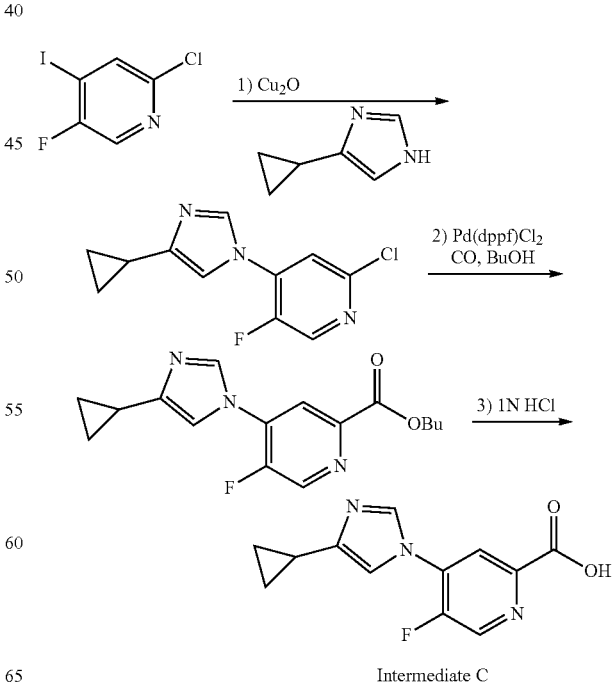

Intermediate C

Step 1: Preparation of 2-chloro-4-(4-cyclopropyl-1H-imidazol-1-yl)-5-fluoropyridine A suspension 2-chloro-5-fluoro-4-iodopyridine (1.8 g, 1.00 mmol), 4-cyclopropyl imidazole (982 mg, 9.10 mmol), $Cu_2O$ (100 mg, 0.700 mmol), 8-hydroxyquinoline (152 mg, 1.05 mmol), cesium carbonate (4.60 g, 14.0 mmol), and PEG-3350 (1.4 g) in butyronitrile (50 mL) was heated at 65° C. for 16 hours. The reaction mixture was filtered through Celite, concentrated and the residue was partitioned between dichlormethane and water. The layers were separated and the aqueous layer washed twice with dichloromethane. The combined organic layers were dried ($MgSO_4$), filtered and concentrated. The residue was purified by flash chromatography (15→60% EtOAc in hexanes) to afford 2-chloro-4-(4-cyclopropyl-1H-imidazol-1-yl)-5-fluoropyridine (702 mg, 42% yield).

Step 2: Preparation of butyl 4-(4-cyclopropyl-1H-imidazol-1-yl)-5-fluoropicolinate 2-chloro-4-(4-cyclopropyl-1H-imidazol-1-yl)-5-fluoropyridine (730 mg, 3.07 mmol) and $Pd(dppf)Cl_2$ (112 mg, 0.159 mmol) were suspended in degassed BuOH, and the reaction vessel was purged with carbon monoxide and a balloon of CO was affixed to the reaction vessel. The mixture was heated to 70° C. for 90 minutes, filtered through Celite, and concentrated. The residue was passed through a short plug of silica gel to afford butyl 4-(4-cyclopropyl-1H-imidazol-1-yl)-5-fluoropicolinate (860 mg, 93%).

Step 3: Preparation of 4-(4-cyclopropyl-1H-imidazol-1-yl)-5-fluoropicolinic Acid 4-(4-cyclopropyl-1H-imidazol-1-yl)-5-fluoropicolinate (640 mg, 2.11 mmol) was dissolved in 1N HCl (5 mL) and the reaction was heated to 100° C. overnight. The solvent was removed, $CH_3CN$ was added and the solvent removed to afford 4-(4-cyclopropyl-1H-imidazol-1-yl)-5-fluoropicolinic acid which was used directly in subsequent reactions (assuming 100% conversion).

Representative Procedure for Amide Coupling Reaction

Preparation of 4-(4-cyclopropyl-1H-imidazol-1-yl)-N-(2-(4-cyclopropyl-4H-1,2,4-triazol-3-yl)thiazol-4-yl)-5-fluoropicolinamide (Intermediate D)

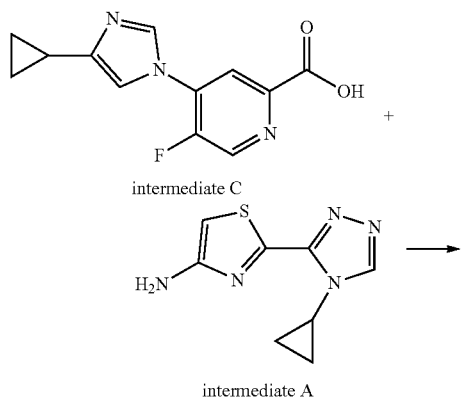

intermediate A

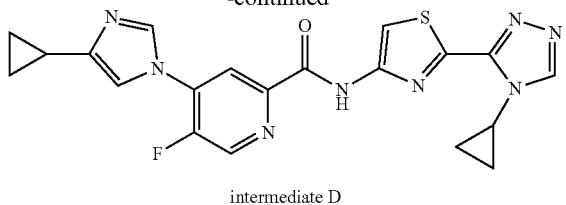

intermediate D

To a mixture of intermediate C.HCl (340 mg, 1.2 mmol), intermediate A (261 mg, 1.26 mmol), HATU (638 mg, 1.68 mmol), and N-methyl morpholine (330 μL, 3.00 mmol) was added DMF (5 mL) and the reaction was stirred for 2 hours. The mixture was concentrated, redissolved in a minimal amount of $CH_3CN$, and water was added dropwise until a thick slurry was formed. The solids were isolated by filtration and washed with $CH_3CN$ to afford 320 mg (61% y). M+1=437.2

Intermediate E was Prepared According to the Same Procedure

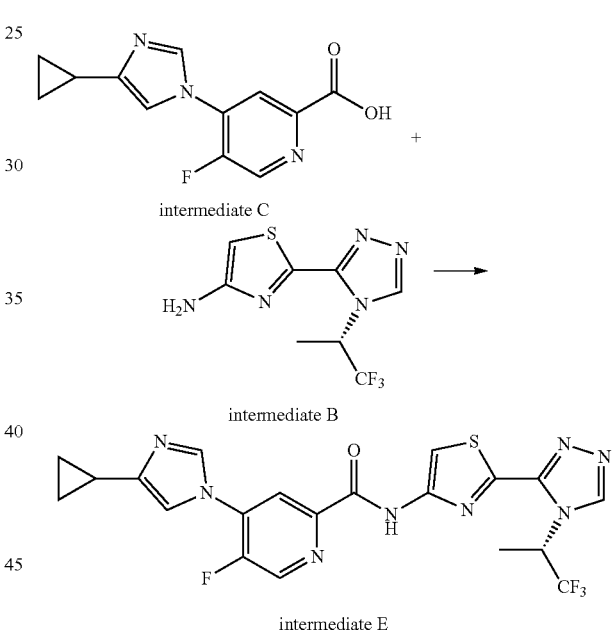

intermediate C intermediate B intermediate E

Representative Procedure for $S_NAr$ Displacement of Aryl Fluoride to Yield Final Products Preparation of 4-(4-cyclopropyl-1H-imidazol-1-yl)-N-(2-(4-cyclopropyl-4H-1,2,4-triazol-3-yl)thiazol-4-yl)-5-morpholinopicolinamide

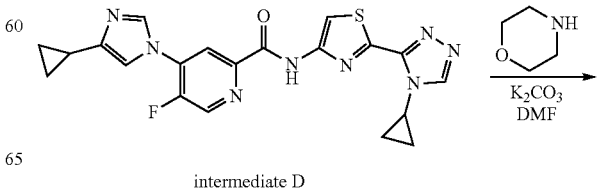

intermediate D

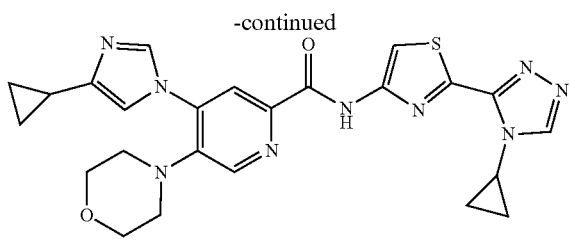

To a mixture of intermediate D (450 mg, 1.03 mmol) and K₂CO₃ (430 mg, 3.09 mmol) in DMF (3 mL) was added morpholine (270 Ld, 3.09 mmol) and the reaction was heated to 80° C. overnight. The reaction was concentrated and purified by RP-HPLC to afford 390 mg (75% y) of 4-(4-cyclopropyl-1H-imidazol-1-yl)-N-(2-(4-cyclopropyl-4H-1,2,4-triazol-3-yl)thiazol-4-yl)-5-morpholinopicolinamide. All final compounds were isolated as the HCl salt from the preparative HPLC.

C₂₄H₂₅N₉O₂S. 504.2. (M+1). ¹H NMR (DMSO) δ 10.99 (s, 1H), 9.57 (s, 1H), 8.79 (s, 1H), 8.64 (s, 1H), 8.27 (s, 1H), 7.99 (s, 2H), 4.05-4.09 (m, 1H), 3.61-3.64 (m, 4H), 2.90-3.05 (m, 4H), 2.04-2.08 (m, 1H), 1.03-1.09 (m, 6H), 0.85-0.90 (m, 2H).

The Following Compounds were Prepared in a Similar Fashion Using the Appropriate Amine and the Indicated Intermediate

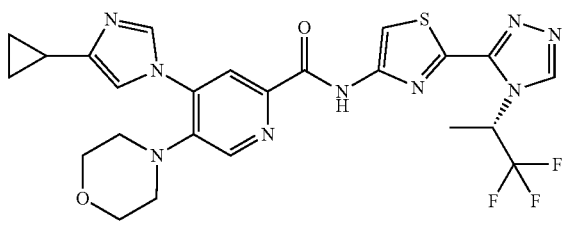 [SMILES: C[C@H](n1cnnc1-c1nc(NC(=O)c2cc(-n3cnc(C4CC4)c3)c(N3CCOCC3)cn2)cs1)C(F)(F)F]

Prepared Via Intermediate D 4-(4-cyclopropyl-1H-imidazol-1-yl)-N-(2-(4-cyclopropyl-4H-1,2,4-triazol-3-yl)thiazol-4-yl)-5-(3-hydroxy-3-methylazetidin-1-yl)picolinamide C₂₄H₂₅N₉O₂S. 504.2. (M+1). ¹H NMR (DMSO) δ 10.74 (s, 1H), 9.32 (s, 1H), 8.76 (s, 1H), 8.14 (s, 1H), 8.10 (s, 1H), 7.93 (s, 1H), 7.77 (s, 1H), 4.02-4.06 (m, 1H), 3.67 (dd, J=8.0, 20.4 Hz, 4H), 2.01-2.06 (m, 1H), 1.37 (s, 3H), 1.03-1.10 (m, 6H), 0.83-0.86 (m, 2H).

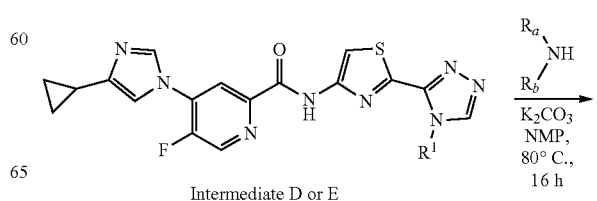

Prepared Via Intermediate E (S)-4-(4-cyclopropyl-1H-imidazol-1-yl)-5-morpholino-N-(2-(4-(1,1,1-trifluoropropan-2-yl)-4H-1,2,4-triazol-3-yl)thiazol-4-yl)picolinamide C₂₄H₂₄F₃N₉O₂S. 560.2. (M+1). ¹H NMR (DMSO) δ 11.46 (s, 1H), 9.56 (s, 1H), 9.23 (s, 1H), 8.64 (s, 1H), 8.27 (s, 1H), 8.01 (s, 1H), 7.99 (s, 1H), 6.78-6.82 (m, 1H), 3.61-3.65 (m, 4H), 2.90-2.94 (m, 4H), 2.02-2.06 (m, 1H), 1.83 (d, J=7.2 Hz, 3H), 1.03-1.07 (m, 2H), 0.86-0.88 (m, 2H).

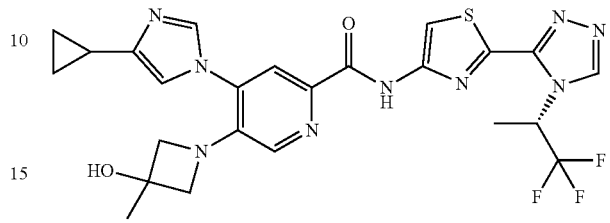

Prepared Via Intermediate E (S)-4-(4-cyclopropyl-1H-imidazol-1-yl)-5-(3-hydroxy-3-methylazetidin-1-yl)-N-(2-(4-(1,1,1-trifluoropropan-2-yl)-4H-1,2,4-triazol-3-yl)thiazol-4-yl)picolinamide C₂₄H₂₄F₃N₉O₂S. 560.1. (M+1). ¹H NMR (DMSO) δ 11.21 (s, 1H), 9.24 (br s, 1H), 9.22 (s, 1H), 8.13 (s, 1H), 8.09 (s, 1H), 7.96 (s, 1H), 7.75 (s, 1H), 6.79 (pent, J=7.2 Hz, 1H), 3.67 (dd, J=8.0, 19.6 Hz, 4H), 2.68 (s, 1H), 2.02-2.05 (m, 1H), 1.82 (d, J=7.2 Hz, 3H), 1.37 (s, 3H), 1.01-1.06 (m, 2H), 0.81-0.85 (m, 2H).

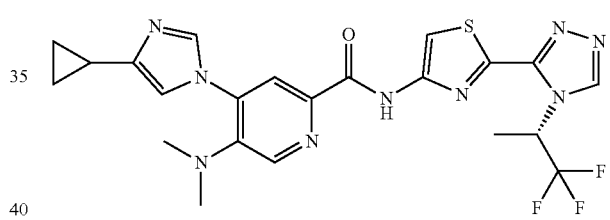

Prepared Via Intermediate E (S)-4-(4-cyclopropyl-1H-imidazol-1-yl)-5-(dimethylamino)-N-(2-(4-(1,1,1-trifluoropropan-2-yl)-4H-1,2,4-triazol-3-yl)thiazol-4-yl)picolinamide C₂₂H₂₂F₃N₉OS. 518.1. (M+1). ¹H NMR (DMSO) δ 11.32 (s, 1H), 9.43 (s, 1H), 9.23 (s, 1H), 8.55 (s, 1H), 8.17 (s, 1H), 7.98 (s, 1H), 7.84 (s, 1H), 6.80 (pent, J=7.2 Hz, 1H), 2.73 (s, 6H), 2.02-2.06 (m, 1H), 1.83 (d, J=7.2 Hz, 3H), 1.01-1.06 (m, 2H), 0.84-0.88 (m, 2H).

Additional General Preparation of Compounds of Formula (I)

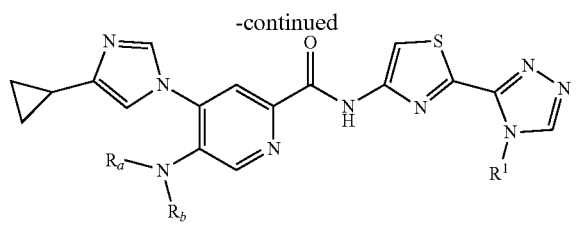

Formula (I)
wherein
R² is H, R³ is H, R⁴ is H
R⁵ is H, R⁶ is cyclopropyl wherein $R^a$, $R^b$, and $R^1$ are defined in formula (I).

In a 2 mL reaction vial was placed the appropriate amine nucleophile (4.1 equivalents) and K₂CO₃ (6.1 equivalents). To this was added a solution of Intermediate D or E (1.0 equivalent) in NMP (0.15 M). The mixture was heated at 80° C. for 16 h. It was cooled to room temperature, and to this was added EtOAc. The resulting supernatant was transferred to a separate collection tube. The solvent was removed by Genevac, and the resulting solid was washed with water and dried to give the desired product. The product identity was verified by LCMS analysis.

Preparation of 4-(4-cyclopropylimidazol-1-yl)-N-[2-(4-cyclopropyl-1,2,4-triazol-3-yl)-1,3-thiazol-4-yl]-5-(3-hydroxypyrrolidin-1-yl)pyridine-2-carboxamide

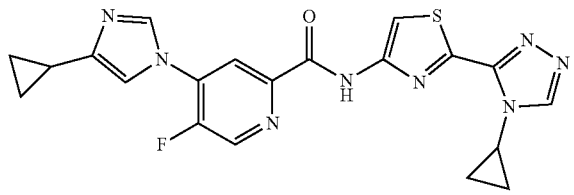 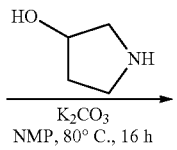

Intermediate D

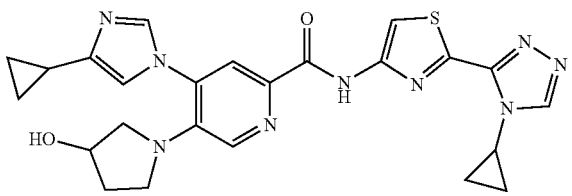

Compound 10

In a 2 ml reaction vial was placed pyrrolidin-3-olhydrochloride (22.7 mg, 0.19 mmol) and K₂CO₃ (38 mg, 0.28 mmol). To this was added a solution of Intermediate D (20 mg, 0.046 mmol) in NMP (0.3 mL). The mixture was heated at 80° C. for 16 h. It was cooled to room temperature, and to this was added EtOAc (1 mL). The solvent was removed by Genevac, and the resulting solid was washed with water and dried to give 4-(4-cyclopropylimidazol-1-yl)-N-[2-(4-cyclopropyl-1,2,4-triazol-3-yl)-1,3-thiazol-4-yl]-5-(3-hydroxypyrrolidin-1-yl)pyridine-2-carboxamide (Compound 10). LRMS (ESI⁺) m/z [M+H]⁺ calcd for C₂₄H₂₆N₉O₂S, 504.2, 504.1.

Compounds 6, 9, 12, 15 and 17 were prepared in a similar fashion using Intermediate D.

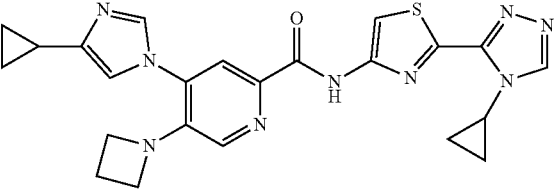 [SMILES: O=C(Nc1csc(-c2nncn2C2CC2)n1)c1cc(-n2cnc(C3CC3)c2)c(N2CCC2)cn1]

5-(azetidin-1-yl)-4-(4-cyclopropylimidazol-1-yl)-N-[2-(4-cyclopropyl-1,2,4-triazol-3-yl)-1,3-thiazol-4-yl]pyridine-2-carboxamide (Compound 6). LRMS (ESI⁺) m/z [M+H]⁺ calcd for C₂₃H₂₃N₉OS 474.2, found: 474.2.

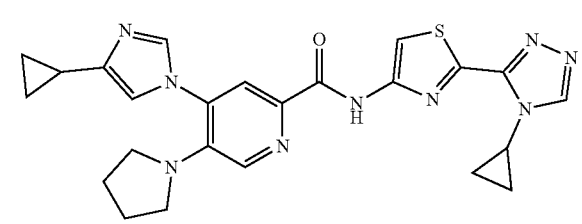 [SMILES: O=C(Nc1csc(-c2nncn2C2CC2)n1)c1cc(-n2cnc(C3CC3)c2)c(N2CCCC2)cn1]

4-(4-cyclopropylimidazol-1-yl)-N-[2-(4-cyclopropyl-1,2,4-triazol-3-yl)-1,3-thiazol-4-yl]-5-pyrrolidin-1-ylpyridine-2-carboxamide (Compound 9). LRMS (ESI⁺) m/z [M+H]⁺ calcd for C₂₄H₂₅N₉OS 488.2, found: 488.2.

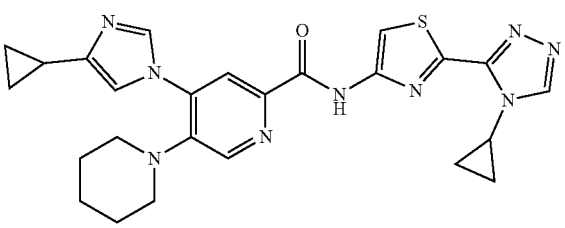 [SMILES: O=C(Nc1csc(-c2nncn2C2CC2)n1)c1cc(-n2cnc(C3CC3)c2)c(N2CCCCC2)cn1]

4-(4-cyclopropylimidazol-1-yl)-N-[2-(4-cyclopropyl-1,2,4-triazol-3-yl)-1,3-thiazol-4-yl]-5-piperidin-1-ylpyridine-2-carboxamide (Compound 12). LRMS (ESI⁺) m/z [M+H]⁺ calcd for C₂₅H₂₇N₉OS 502.2, found: 502.1.

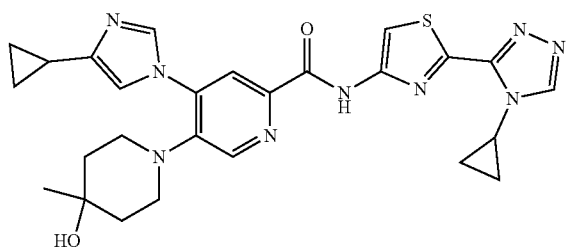 [SMILES: CC1(O)CCN(c2cnc(C(=O)Nc3csc(-c4nncn4C4CC4)n3)cc2-n2cnc(C3CC3)c2)CC1]

4-(4-cyclopropylimidazol-1-yl)-N-[2-(4-cyclopropyl-1,2,4-triazol-3-yl)-1,3-thiazol-4-yl]-5-(4-hydroxy-4-methylpiperidin-1-yl)pyridine-2-carboxamide (Compound 15). LRMS (ESI$^+$) m/z [M+H]$^+$ calcd for $C_{26}H_{29}N_9O_2S$, 532.2, found: 532.1.

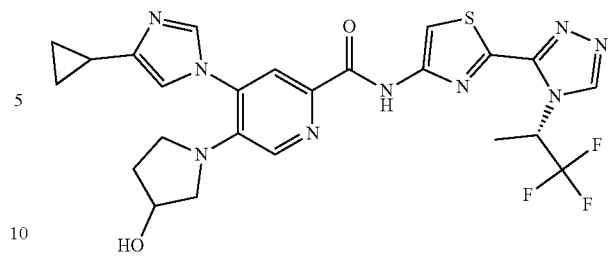

4-(4-cyclopropyl-1H-imidazol-1-yl)-5-(3-hydroxypyrrolidin-1-yl)-N-(2-(4-((S)-1,1,1-trifluoropropan-2-yl)-4H-1,2,4-triazol-3-yl)thiazol-4-yl)picolinamide (Compound 11). LRMS (ESI$^+$) m/z [M+H]$^+$ calcd for $C_{24}H_{24}F_3N_9O_2S$, 560.2, found: 560.2.

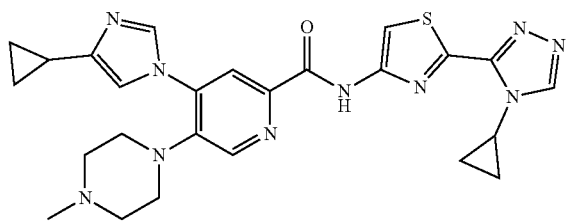 [SMILES: CN1CCN(c2cnc(C(=O)Nc3csc(-c4nncn4C4CC4)n3)cc2-n2cnc(C3CC3)c2)CC1]

4-(4-cyclopropylimidazol-1-yl)-N-[2-(4-cyclopropyl-1,2,4-triazol-3-yl)-1,3-thiazol-4-yl]-5-(4-methylpiperazin-1-yl)pyridine-2-carboxamide (Compound 17). LRMS (ESI$^+$) m/z [M+H]$^+$ calcd for $C_{25}H_{28}N_{10}OS$ 517.2, found: 517.1.

Compounds 7, 8, 11, 13, 14, and 16 were prepared in similar general preparation procedure using Intermediate E.

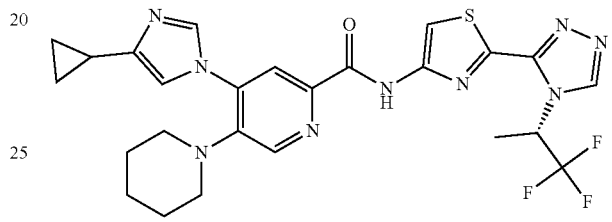

(S)-4-(4-cyclopropyl-1H-imidazol-1-yl)-5-(piperidin-1-yl)-N-(2-(4-(1,1,1-trifluoropropan-2-yl)-4H-1,2,4-triazol-3-yl)thiazol-4-yl)picolinamide (Compound 13). LRMS (ESI$^+$) m/z [M+H]$^+$ calcd for $C_{25}H_{26}F_3N_9OS$ 558.2, found: 557.9.

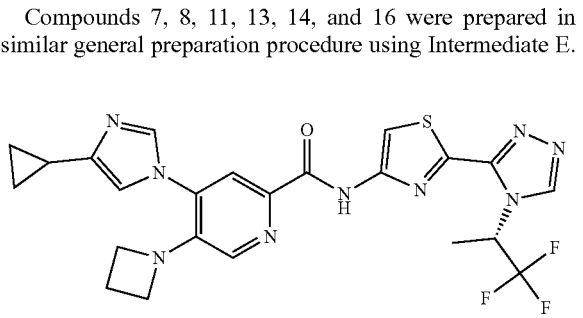

(S)-5-(azetidin-1-yl)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide (Compound 7). LRMS (ESI$^+$) m/z [M+H]$^+$ calcd for $C_{23}H_{22}F_3N_9OS$ 530.2, found: 530.2.

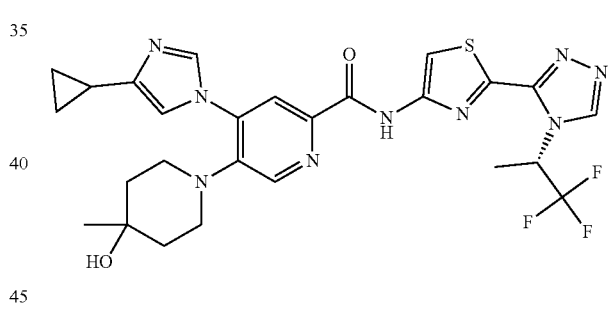

(S)-4-(4-cyclopropyl-1H-imidazol-1-yl)-5-(4-hydroxy-4-methylpiperidin-1-yl)-N-(2-(4-(1,1,1-trifluoropropan-2-yl)-4H-1,2,4-triazol-3-yl)thiazol-4-yl)picolinamide (Compound 14). LRMS (ESI$^+$) m/z [M+H] calcd for $C_{26}H_{28}F_3N_9O_2S$, 588.2, found: 587.9.

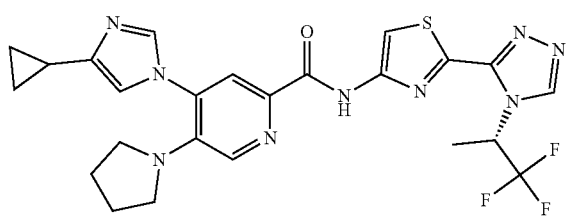 [SMILES: C[C@H](n1cnnc1-c1nc(NC(=O)c2cc(-n3cnc(C4CC4)c3)c(N3CCCC3)cn2)cs1)C(F)(F)F]

(S)-4-(4-cyclopropyl-1H-imidazol-1-yl)-5-(pyrrolidin-1-yl)-N-(2-(4-(1,1,1-trifluoropropan-2-yl)-4H-1,2,4-triazol-3-yl)thiazol-4-yl)picolinamide (Compound 8). LRMS (ESI$^+$) m/z [M+H]$^+$ calcd for $C_{24}H_{24}F_3N_9OS$ 544.2, found: 543.8.

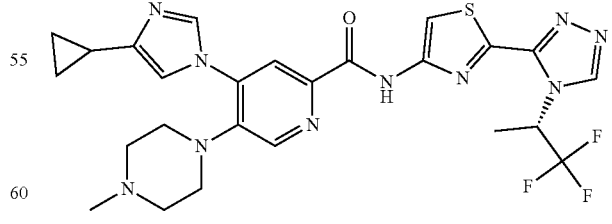

(S)-4-(4-cyclopropyl-1H-imidazol-1-yl)-5-(4-methylpiperazin-1-yl)-N-(2-(4-(1,1,1-trifluoropropan-2-yl)-4H-1,2,4-triazol-3-yl)thiazol-4-yl)picolinamide (Compound 16) LRMS (ESI$^+$) m/z [M+H]$^+$ calcd for $C_{25}H_{27}F_3N_{10}OS$ 573.2, found: 573.1.

Utility, Testing and Administration

General Utility

The compounds of Formula I are believed effective in the treatment of conditions that respond to administration of ASK1 inhibitors. Specifically, the compounds of Formula I are useful in the treatment of a broad range of diseases, for example autoimmune disorders, inflammatory diseases, cardiovascular diseases (including diabetes, diabetic nephropathy, and other complications of diabetes), cardio-renal diseases, including kidney disease, fibrotic diseases, respiratory diseases (including COPD, idiopathic pulmonary fibrosis (IPF), and acute lung injury), acute and chronic liver diseases, and neurodegenerative diseases.

Testing

Activity testing is conducted as described in the Examples below, and by methods apparent to one skilled in the art.

The following examples are included to demonstrate preferred embodiments of the invention. It will be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Biological Assays

To evaluate the inhibitory activity of compounds of the invention against ASK1 (Apoptosis Signal-regulating Kinase 1) kinase, its activity was examined using a TR-FRET ASK1 kinase assay which determined the amount of phosphate transferred to a peptide substrate from ATP.

Materials and Methods

Reagents

Dephosphorylated recombinant human ASK1 kinase was from Gilead Sciences. Small molecule kinase inhibitor staurosporine (Catalogue # S6942) and dithiothreitol (DTT, catalogue #43815-5G) were obtained from Sigma Chemicals (St. Louis, Mo.). ATP (catalogue #7724) was from Affymetrix (Santa Clara, Calif.) and test compounds were from Gilead Sciences. HTRF KinEASE™-STK S3 kit was obtained from Cisbio (Bedford, Mass.). All other reagents were of the highest grade commercially available.

Assays

The assay measures the phosphorylation level of a biotinylated peptide substrate by the ASK1 kinase using HTRF detection (6.1). This is a competitive, time-resolved fluorescence resonance energy transfer (TR-FRET) immunoassay, based on HTRF® KinEASE™-STK manual from Cisbio (6.1). Test compound, 1 µM STK3 peptide substrate, 4 nM of ASK1 kinase are incubated with 10 mM MOP buffer, pH. 7.0 containing 10 mM Mg-acetate, 0.025% NP-40, 1 mM DTT, 0.05% BSA and 1.5% glycerol for 30 minutes then 100 µM ATP is added to start the kinase reaction and incubated for 3 hr. Peptide antibody labeled with 1×Eu$^{3+}$ Cryptate buffer containing 10 mM EDTA and 125 nM Streptavidin XL665 are added to stop the reaction and phosphorylated peptide substrate is detected using Envision 2103 Multilabeled reader from PerkinElmer. The fluorescence is measured at 615 nm (Cryptate) and 665 nm (XL665) and a ratio of 665 nm/615 nm is calculated for each well. The resulting TR-FRET level (a ratio of 665 nm/615 nm) is proportional to the phosphorylation level. Under these assay conditions, the degree of phosphorylation of peptide substrate was linear with time and concentration of the enzyme. The assay system yielded consistent results with regard to $K_m$ and specific activities for the enzyme. For inhibition experiments ($IC_{50}$ values), activities were performed with constant concentrations of ATP, peptide and several fixed concentrations of inhibitors. Staurosporine, the nonselective kinase inhibitor, was used as the positive control. All enzyme activity data are reported as an average of quadruplicate determination.

Data Analysis

The $IC_{50}$ values were calculated following equation:

$$y = \text{Range}/\{1+(x/IC_{50})^s\}+\text{Background}$$

Where x and y represent the concentration of inhibitors and enzyme activity, respectively. Enzyme activity is expressed as the amount of Phosphate incorporated into substrate peptide from ATP. Range is the maximum y range (no inhibitor, DMSO control) and s is a slope factor (6.2).

Results

Following the above method, tested compounds of Formula (I) inhibited ASK1 as shown below.

| Example # | Compound name | ASK1 $IC_{50}$ (nM) |
|---|---|---|
| 1 | 4-(4-cyclopropyl-1H-imidazol-1-yl)-N-(2-(4-cyclopropyl-4H-1,2,4-triazol-3-yl)thiazol-4-yl)-5-morpholinopicolinamide | 1.44 |
| 2 | 4-(4-cyclopropyl-1H-imidazol-1-yl)-N-(2-(4-cyclopropyl-4H-1,2,4-triazol-3-yl)thiazol-4-yl)-5-(3-hydroxy-3-methylazetidin-1-yl)picolinamide | 1.58 |
| 3 | (S)-4-(4-cyclopropyl-1H-imidazol-1-yl)-5-morpholino-N-(2-(4-(1,1,1-trifluoropropan-2-yl)-4H-1,2,4-triazol-3-yl)thiazol-4-yl)picolinamide | 2.62 |
| 4 | (S)-4-(4-cyclopropyl-1H-imidazol-1-yl)-5-(3-hydroxy-3-methylazetidin-1-yl)-N-(2-(4-(1,1,1-trifluoropropan-2-yl)-4H-1,2,4-triazol-3-yl)thiazol-4-yl)picolinamide | 1.69 |
| 5 | (S)-4-(4-cyclopropyl-1H-imidazol-1-yl)-5-(dimethylamino)-N-(2-(4-(1,1,1-trifluoropropan-2-yl)-4H-1,2,4-triazol-3-yl)thiazol-4-yl)picolinamide | 1.88 |
| Staurosporine | | 6.30 |

The data demonstrates that tested compounds of formula (I) are potent inhibitors of the ASK-1 receptor.

ASK1 (Apoptosis Signal-Regulating Kinase 1) 293 Cell-Based Assay (Cellular $EC_{50}$)

The cellular potency of compounds was assayed in cells stably expressing an AP-1:luciferase reporter construct (293/AP1-Luc cells—Panomics Inc., 6519 Dumbarton Circle, Fremont, Calif.). Cells were infected with an adenovirus expressing kinase active ASK1 (631-1381 of rat ASK1 cDNA), which will activate the AP-1 transcription factor and increase the expression of luciferase. Inhibitors of ASK1 will decrease the enzyme activity of ASK1 and therefore decrease the activity of AP-1 transcription factor and the expression of luciferase.

1. Materials Required for this Protocol

| Media and Reagents | Source Company | Catalog No. |
|---|---|---|
| AP-1 Reporter 293 Stable Cell Line | Panomics | Unknown |
| DMEM (w/ high glucose, w/o L-glutamine, w/ pyruvate, w/ HEPES | MediaTech | 15-018-CM |

-continued

| Reagent | Source | Catalog No. |
|---|---|---|
| DMEM (w/ high glucose, w/o L-glutamine, w/o pyruvate, w/o HEPES, w/o phenol red | Invitrogen | 31053-028 |
| HEPES, 1M | Invitrogen | 15630-080 |
| Sodium Pyruvate, 100 mM | Invitrogen | 11360-070 |
| Fetal Bovine Serum, "FBS" | Hyclone | SH30088.03 |
| Pen-Strep-Glut., "PSG" | Invitrogen | 10378-016 |
| HygromycinB | Calbiochem | 400052 |
| Dulbecco's PBS (sterile) | MediaTech | 21-030-CM |
| Trypsin-EDTA (0.25%) | Invitrogen | 25200-056 |
| Steady-Glo Luciferase Assay System | Promega | E2550 |

| Labware | Source | Catalog No. |
|---|---|---|
| Flasks (poly-D-Lysine coated, 150 cm$^2$, vented cap) | BD Biosciences | 356538 |
| Plates (poly-D-Lysine coated, 384-well, white/clear, sterile TCT) | Greiner (through VWR Scientific) | 781944 (82051-354) |
| White Backing Tape | PerkinElmer | 6005199 |
| Cell Strainers (40 um nylon, blue ring, fits 50 mL conical vials) | VWR Scientific | 21008-949 |

2. Reference Materials
1. Panomics 293/AP1-Luc stable cell-line product insert.
2. Promega Steady-Glo Luciferase Assay System product insert.
3. Media Required
3. Complete Growth Medium, "CGM"
a. DMEM (MediaTech)
b. 10% FBS
c. 1% PSG
d. 100 ug/mL HygromycinB
4. Assay Medium, "AM"
a. DMEM (Invitrogen)
b. 25 mM HEPES
c. 1 mM Sodium Pyruvate
d. 1% PSG
4. Methods
Maintenance:
1. 293/AP1-Luc Maintain 293/Acells per vendor's instructions; harvest cells at ~80% confluence in T150 flasks as follows:
a. Aspirate media, wash gently with ~12 mL sterile D-PBS, aspirate.
b. Add 5 mL Trypsin-EDTA, tilt gently to coat flask, and incubate ~5 min. at 37° C.
c. Do not tap flask; add 5 mL CGM, wash flask 4× with cell suspension, transfer to 50 mL conical vial, centrifuge 5 min. at 1200 rpm.
d. Aspirate media from cell pellet, add 20 to 30 mL CGM, resuspend pellet by pipetting 6×, pass through cell strainer to disperse clumps (if necessary), and count cells with hemocytometer.
Assay Day 1:
2. Harvest cells as above, except resuspend cell pellet.
Count cells and dilute to 1.5×10$^5$ cells per mL; add adenovirus such that there are 5 infectious forming units per cell.
3. Prime (20 to 30 mL) and plate cells in Greiner poly-D-Lysine coated 384-well plates at 1.2×10$^4$ cells per well using BioTek uFill (80 uL per well).
4. Immediately dose plates with 0.4 uL of compound dose series (in 100% DMSO) incubate 24 hours in humidified incubator (37° C., 5% CO$_2$).

Assay Day 2:
5. Process plates (per manufacturer's instructions) as follows:
a. Set plates in laminar flow hood & uncover for 30 minutes at room temperature to cool.
b. Remove 60 uL of AM from assay wells
c. Add 20 uL per well Steady-Glo Firefly substrate, let sit for 10-20 minutes at room temperature
d. Cover bottom of assay plates with white backing tape.
e. Acquire data on a fluorescence plate reader
The 100% inhibition positive control wells were generated by infecting cells with an adenovirus expressing catalytically inactive ASK1 mutant with lysine to argine mutation at residue 709.
Result

| Example # | Compound name | ASK1 EC50 (nM) |
|---|---|---|
| 1 | 4-(4-cyclopropyl-1H-imidazol-1-yl)-N-(2-(4-cyclopropyl-4H-1,2,4-triazol-3-yl)thiazol-4-yl)-5-morpholinopicolinamide | 13.15 |
| 2 | 4-(4-cyclopropyl-1H-imidazol-1-yl)-N-(2-(4-cyclopropyl-4H-1,2,4-triazol-3-yl)thiazol-4-yl)-5-(3-hydroxy-3-methylazetidin-1-yl)picolinamide | 11.17 |
| 3 | (S)-4-(4-cyclopropyl-1H-imidazol-1-yl)-5-morpholino-N-(2-(4-(1,1,1-trifluoropropan-2-yl)-4H-1,2,4-triazol-3-yl)thiazol-4-yl)picolinamide | 6.74 |
| 4 | (S)-4-(4-cyclopropyl-1H-imidazol-1-yl)-5-(3-hydroxy-3-methylazetidin-1-yl)-N-(2-(4-(1,1,1-trifluoropropan-2-yl)-4H-1,2,4-triazol-3-yl)thiazol-4-yl)picolinamide | 5.21 |
| 5 | (S)-4-(4-cyclopropyl-1H-imidazol-1-yl)-5-(dimethylamino)-N-(2-(4-(1,1,1-trifluoropropan-2-yl)-4H-1,2,4-triazol-3-yl)thiazol-4-yl)picolinamide | 7.12 |

The above data suggests that compounds of formula (I), particularly compounds tested exhibit potent in-vitro efficacy.
Human Whole Blood CXCL1 Assay
Reagents
Human blood collected in sodium heparin glass vacutainer tubes (BD Biosciences #366480) was obtained from Stanford Blood Center (Palo Alto, Ca). Red blood cell Ammonium-Chloride-Potassium (ACK) lysis buffer was obtained from Invitrogen (A10492-01) Phosphate buffered saline (PBS, 21-031-CV) and RPMI640 media (10-040-CV) were purchased from Cellgro. 50 ml conical tubes were from BD Biosciences (352070). Multiscreen Filter plates (MS-BVS 1210) used along with vacuum manifold for 96-well plate (MAVM0960R) were purchased from EMD Millipore Inc. Transfer pipettes (13-711-20) and hemocytometer (0267110) were purchased from Thermo Fisher Scientific. An Allegra X15R from Beckmann Coulter was used for all the centrifugation steps in the isolation of PBMCs.
ASK1 inhibitors and Auranofin (Enzo Life Sciences Inc. BML-EI206-0100) were dissolved in dimethyl sulfoxide (DMSO, Sigma Aldrich cat#472301) at a concentration of 10 mM and 100 mM, respectively. Aliquots were stored frozen at −20° C. until the time of use and not reused or refrozen. Serial dilutions of ASK1 inhibitors were preformed in saline (pH 4.5-7, Hospira Inc, RL-2099). Cell Extraction buffer (FNN0011) and Halt protease/phosphatase inhibitor cocktail (78442) were purchased from Life Technologies, Inc. and Thermofisher Scientific Inc., respectively.

A Boekel scientific Rocker II was used to agitate the plates between treatments. CXCL1 protein was quantified with an ELISA assay from Millipore.

Compound Treatment and Auranofin Stimulation

A 10 mM ASK1 inhibitor DMSO stock was diluted in saline to create a 100 µM (10×) working solution. This was subjected to an eight point, three-fold serial dilution series in saline, with each concentration at 10× the final intended concentration. 10 uL of each 10× working stock was added to eight wells of a 96 plate containing 90 µl of whole blood, creating a dose range of 10 uM to 1.5 nM (Final assay plate configuration shown below) with eight replicates per concentration. The samples were incubated for one hour in a 37° C. and 5% $CO_2$ incubator. A 100 mM Auranofin stock was diluted to 100 µM in RPMI media and 5 ul was added to each well of the assay plate to make a final concentration of approximately 5 µM. In control samples that were not treated with Ask1 inhibitor or Auranofin, DMSO/saline were added at equivalent amounts as the wells incubated with the highest concentration of test compound (0.1% final concentration of DMSO). The samples were incubated in a 37° C./5% $CO_2$ incubator for 24 hours with gentle agitation. At the end of the incubation period, 100 µl of RPMI 1640 media was added to each well, and the plates were gently mixed and then centrifuged at 1000×g for 10 min at 4° C. to pellet the cells. 50 µl of the resulting supernatant from each well was transferred to a new 96 well assay plate and the amount of CXCL1 was quantified by a Procarta immunoassay following the manufacturer's instructions. Each compound was tested in blood from at least two independent donors.

Final Assay Plate Configuration

| Test Compound µM | 0 | 0 | 0.0045 | 0.014 | 0.041 | 0.12 | 0.37 | 1.1 | 3.3 | 10 |
|---|---|---|---|---|---|---|---|---|---|---|
| Auranofin µM | 0 | 5 | 5 | 5 | 5 | 5 | 5 | 5 | 5 | 5 |

Replicate 1
Replicate 2
Replicate 3
Replicate 4
Replicate 5
Replicate 6
Replicate 7
Replicate 8

Data Analysis

Data was analyzed using GraphPad Prism 5 software (GraphPad Software Inc., La Jolla, Calif., USA) using nonlinear regression curve fitting with variable slope to determine the $EC_{50}$ values. The average $EC_{50}$ from at least two independent donors is reported.

Results:

| Example No. | Compound Name | WB EC50 nM (n = 4) |
|---|---|---|
| 1 | 4-(4-cyclopropyl-1H-imidazol-1-yl)-N-(2-(4-cyclopropyl-4H-1,2,4-triazol-3-yl)thiazol-4-yl)-5-morpholinopicolinamide | 243 |
| 3 | (S)-4-(4-cyclopropyl-1H-imidazol-1-yl)-5-morpholino-N-(2-(4-(1,1,1-trifluoropropan-2-yl)-4H-1,2,4-triazol-3-yl)thiazol-4-yl)picolinamide | 202 |

The data suggests that compounds of formula (I) are potent in vivo inhibitors of ASK1. The activities of Compounds 6-17 were examined using the assay measures the phosphorylation level of a biotinylated peptide substrate by the ASK1 kinase using the same competitive TR-FRET immunoassay based on HTRF® KinEASE™-STK manual from Cisbio (6.1) as described above. The tested compounds inhibited ASK1 as shown below.

| Example # | Compound name | ASK1 $IC_{50}$ (nM) |
|---|---|---|
| 6 | 5-(azetidin-1-yl)-4-(4-cyclopropylimidazol-1-yl)-N-[2-(4-cyclopropyl-1,2,4-triazol-3-yl)-1,3-thiazol-4-yl]pyridine-2-carboxamide | 2.4 |
| 7 | (S)-5-(azetidin-1-yl)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide | 1.7 |
| 8 | (S)-4-(4-cyclopropyl-1H-imidazol-1-yl)-5-(pyrrolidin-1-yl)-N-(2-(4-(1,1,1-trifluoropropan-2-yl)-4H-1,2,4-triazol-3-yl)thiazol-4-yl)picolinamide | 2.2 |
| 9 | 4-(4-cyclopropylimidazol-1-yl)-N-[2-(4-cyclopropyl-1,2,4-triazol-3-yl)-1,3-thiazol-4-yl]-5-pyrrolidin-1-ylpyridine-2-carboxamide | 1.9 |
| 10 | 4-(4-cyclopropylimidazol-1-yl)-N-[2-(4-cyclopropyl-1,2,4-triazol-3-yl)-1,3-thiazol-4-yl]-5-(3-hydroxypyrrolidin-1-yl)pyridine-2-carboxamide | 3 |
| 11 | 4-(4-cyclopropylimidazol-1-yl)-5-(3-hydroxypyrrolidin-1-yl)-N-[2-[4-(1,1,1-trifluoropropan-2-yl)-1,2,4-triazol-3-yl]-1,3-thiazol-4-yl]pyridine-2-carboxamide | 2.2 |
| 12 | 4-(4-cyclopropylimidazol-1-yl)-N-[2-(4-cyclopropyl-1,2,4-triazol-3-yl)-1,3-thiazol-4-yl]-5-piperidin-1-ylpyridine-2-carboxamide | 2 |
| 13 | (S)-4-(4-cyclopropyl-1H-imidazol-1-yl)-5-(piperidin-1-yl)-N-(2-(4-(1,1,1-trifluoropropan-2-yl)-4H-1,2,4-triazol-3-yl)thiazol-4-yl)picolinamide | 0.7 |
| 14 | 4-(4-cyclopropylimidazol-1-yl)-5-(4-hydroxy-4-methylpiperidin-1-yl)-N-[2-[4-(1,1,1-trifluoropropan-2-yl)-1,2,4-triazol-3-yl]-1,3-thiazol-4-yl]pyridine-2-carboxamide | 1.8 |
| 15 | 4-(4-cyclopropylimidazol-1-yl)-N-[2-(4-cyclopropyl-1,2,4-triazol-3-yl)-1,3-thiazol-4-yl]-5-(4-hydroxy-4-methylpiperidin-1-yl)pyridine-2-carboxamide | 2.5 |
| 16 | (S)-4-(4-cyclopropyl-1H-imidazol-1-yl)-5-(4-methylpiperazin-1-yl)-N-(2-(4-(1,1,1-trifluoropropan-2-yl)-4H-1,2,4-triazol-3-yl)thiazol-4-yl)picolinamide | 2.1 |
| 17 | 4-(4-cyclopropylimidazol-1-yl)-N-[2-(4-cyclopropyl-1,2,4-triazol-3-yl)-1,3-thiazol-4-yl]-5-(4-methylpiperazin-1-yl)pyridine-2-carboxamide | 3.1 |

The data demonstrates that tested compounds of formula (I) are potent inhibitors of the ASK-1 receptor.

What is claimed is:

1. A compound having the structure:

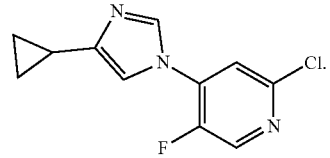 [SMILES: Fc1cnc(Cl)cc1-n1cnc(C2CC2)c1]

* * * * *